＝

US008394031B2

(12) United States Patent
Mansy et al.

(10) Patent No.: US 8,394,031 B2
(45) Date of Patent: Mar. 12, 2013

(54) ACOUSTIC DETECTION OF ENDOTRACHEAL TUBE LOCATION

(75) Inventors: Hansen A. Mansy, Justice, IL (US); Richard H. Sandler, Evanston, IL (US)

(73) Assignee: Biomedical Acoustic Research, Corp., Evanston, IL (US)

( * ) Notice: Subject to any disclaimer, the term of this patent is extended or adjusted under 35 U.S.C. 154(b) by 2503 days.

(21) Appl. No.: 10/186,763

(22) Filed: Jul. 1, 2002

(65) Prior Publication Data

US 2003/0018276 A1 Jan. 23, 2003

Related U.S. Application Data

(63) Continuation-in-part of application No. 09/684,068, filed on Oct. 6, 2000, now Pat. No. 6,443,907.

(51) Int. Cl.
*A61B 5/06* (2006.01)
(52) U.S. Cl. ........................................ 600/550; 600/586
(58) Field of Classification Search .................. 600/532, 600/513, 586, 550, 508–509, 528–529; 381/67, 381/92
See application file for complete search history.

(56) References Cited

U.S. PATENT DOCUMENTS

| | | | | |
|---|---|---|---|---|
| 3,990,435 A | * | 11/1976 | Murphy | 600/529 |
| 4,672,977 A | * | 6/1987 | Kroll | 600/528 |
| 4,817,149 A | * | 3/1989 | Myers | 381/1 |
| 4,951,678 A | * | 8/1990 | Joseph et al. | 600/484 |
| 5,259,384 A | * | 11/1993 | Kaufman et al. | 600/442 |
| 5,301,679 A | * | 4/1994 | Taylor | 600/586 |
| 5,331,967 A | * | 7/1994 | Akerson | 600/529 |
| 5,445,144 A | * | 8/1995 | Wodicka et al. | 128/207.14 |
| 5,535,739 A | * | 7/1996 | Rapoport et al. | 128/204.23 |
| 5,685,317 A | * | 11/1997 | Sjostrom | 600/528 |
| 5,844,997 A | * | 12/1998 | Murphy, Jr. | 381/92 |
| 5,928,156 A | * | 7/1999 | Krumbiegel et al. | 600/529 |
| 6,139,505 A | * | 10/2000 | Murphy | 600/532 |
| 6,168,568 B1 | * | 1/2001 | Gavriely | 600/529 |
| 6,183,423 B1 | * | 2/2001 | Gaumond et al. | 600/529 |
| 6,349,720 B1 | * | 2/2002 | Clark | 128/200.26 |
| 6,383,142 B1 | * | 5/2002 | Gavriely | 600/529 |
| 6,440,082 B1 | * | 8/2002 | Joo et al. | 600/528 |
| 6,449,586 B1 | * | 9/2002 | Hoshuyama | 702/190 |
| 6,699,204 B1 | * | 3/2004 | Kehyayan et al. | 600/533 |

OTHER PUBLICATIONS

PCT International Preliminary Examining Authority, International Preliminary Examination Report for International Application No. PCT/US03/20674, 1-4 (Aug. 10, 2004).

* cited by examiner

*Primary Examiner* — Rene Towa
(74) *Attorney, Agent, or Firm* — Hanley, Flight & Zimmerman, LLC

(57) ABSTRACT

A system and method for use in detecting an endotracheal tube location within a body electronically detects indigenous breath sounds emanating from a region of the body and processes the detected indigenous breath sounds to generate a parameter representative of an acoustic characteristic of the body associated with the endotracheal tube location within the body. The system and method generates an output indicative of the endotracheal tube location within the body based on the parameter representative of the acoustic characteristic of the body.

48 Claims, 17 Drawing Sheets

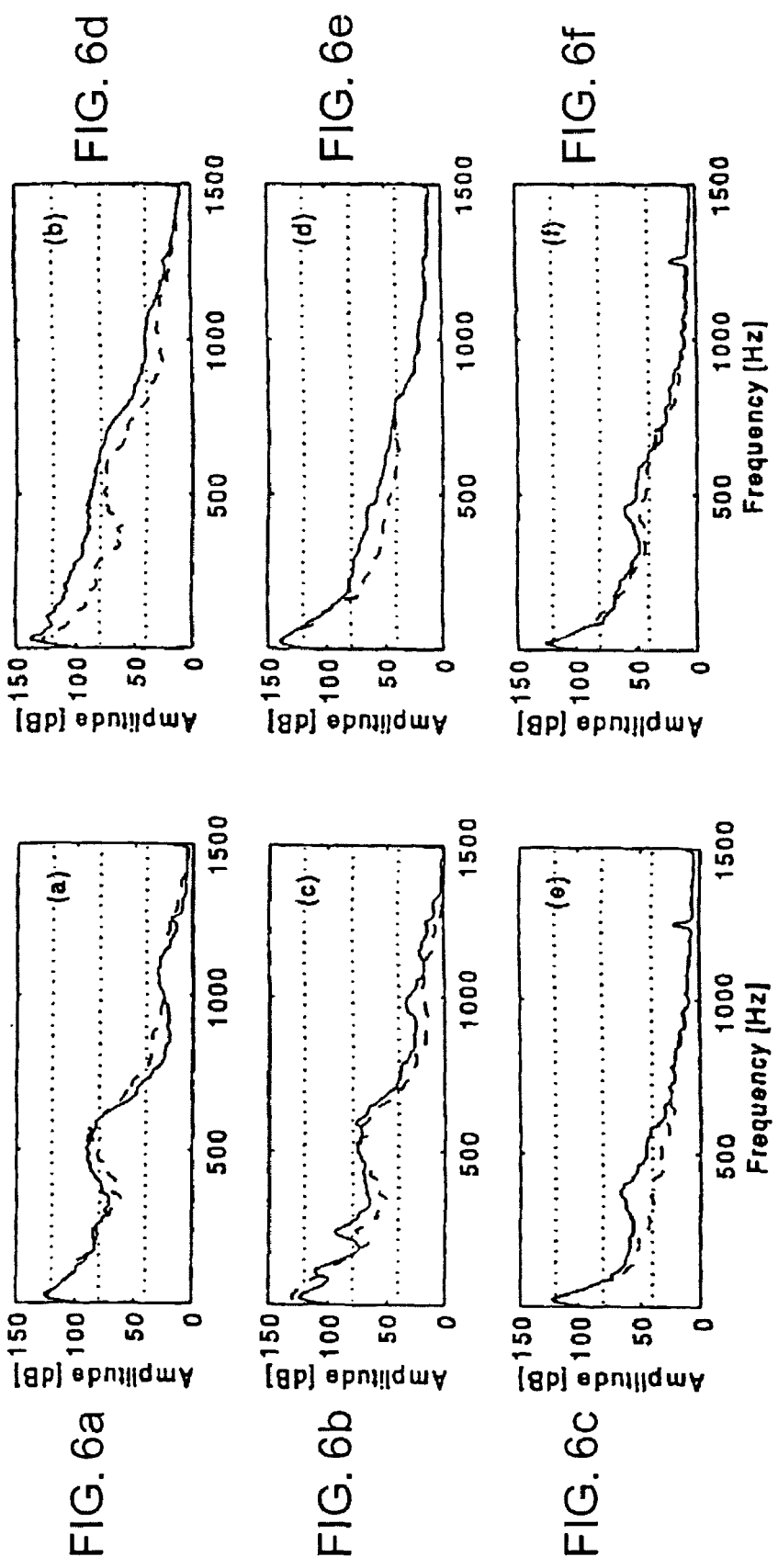

ACOUSTIC DETECTION OF ENDOTRACHEAL TUBE LOCATION

RELATED APPLICATION

This application is a continuation-in-part of U.S. patent application Ser. No. 09/684,068 entitled "Acoustic Detection of Respiratory Conditions," which was filed on Oct. 6, 2000, and is now issued as U.S. Pat. No. 6,443,907, which is hereby incorporated by reference herein in its entirety.

BACKGROUND OF THE INVENTION

1. Field of the Invention

The invention relates generally to the non-invasive diagnosis of conditions within a human or animal body and, more particularly, the invention relates to a diagnostic system and techniques that use the acoustic characteristics within a body to detect the location of an endotracheal tube therein.

2. Description of Related Technology

One particularly problematic respiratory condition is pneumothorax. Generally speaking, pneumothorax refers to the formation of a gas cavity between one or both lungs and the chest wall. As is well known, pneumothorax has many potential causes, including, for example, spontaneous rupture of small alveoli or blebs, progression of inflammatory diseases, complications of diagnostic or therapeutic procedures, penetrating wounds caused by a knife, bullet, etc. and blunt chest trauma, which may be, for example, caused by motor vehicle accidents. Although trauma is a significant cause of pneumothorax, severe chest wall injury is often difficult to detect based on the outward appearance of a patient's body and, as a result, the diagnosis of pneumothorax is often missed in these cases.

Pneumothorax also occurs in 5-15% of mechanically ventilated patients, and other iatrogenic pneumothoraces are becoming more common with the increasing use of chest invasive procedures such as central venous line insertions, which are often used for monitoring and fluid replacement in emergency trauma cases, and percutaneous transthoracic lung biopsies. For these invasive procedures, the pneumothorax rates are about 5% and 20%, respectively. It is estimated that over 50,000 cases of pneumothorax occur each year in the United States and, thus, more effective diagnosis of pneumothorax could significantly reduce morbidity and mortality.

Conventional pneumothorax diagnostic techniques are typically based on patient history, physical examination of the patient, chest x-rays (CXRs), computerized tomogram (CT) and ultrasound. Patient history, physical examination and CXRs are the techniques most commonly employed to diagnose pneumothorax. Unfortunately, patient history and physical examination are typically unreliable techniques for diagnosing pneumothorax because the symptoms associated with pneumothorax are also present in a number of unrelated clinical conditions such as cardiac ischemia, pneumonia, pulmonary embolism, esophageal spasm/reflux, and musculoskeletal strain. As a result, diagnosis of pneumothorax based on patient history and/or physical examination is very difficult and, in many cases, virtually impossible. For example, one study reported that physical examinations resulted in misdiagnosis in 42% of patients having a pneumothorax condition that arose from a penetrating chest wound.

Percussion is one common physical examination technique used by physicians to diagnose a variety of chest abnormalities. Most studies of percussion rely on qualitative descriptions such as "dull" and "resonant" to describe the chest sounds resulting from a percussive input to the patient's chest. Reported percussion response waveforms of a normal chest are typically 20 milliseconds (ms) long and contain an initial spike followed by a decaying waveform with spectral peaks in the 70 Hertz (Hz) to 200 Hz range. Using percussion, skilled physicians have noted "hyperresonance" as an acoustic phenomenon that is often heard in patients having a pneumothorax condition. In addition, acoustic asymmetries with large pneumothoraces have been reported when manually percussing both clavicles in turn while auscultating (i.e., listening to) the sternum. In any event, despite widespread belief in the usefulness of percussive techniques, uncertainty of its diagnostic capability exits because of the inherent dependence on the skill of the operator and their personal perception of the sound qualities of a patient's chest response.

Misdiagnosis of pneumothorax may also occur when using CXRs and CT due to large bullae and cysts within the lung or pleural space, patient clothing, tubing, skin folds, and chest wall artifacts. Additionally, with CXRs, patients are exposed to potentially harmful doses of radiation. Unfortunately, the radiation problem is compounded by the fact that CXRs are often performed unnecessarily (which needlessly exposes patients to radiation) because physicians are unwilling to miss the diagnosis due to the life threatening nature of pneumothorax, the tendency of pneumothorax to progress rapidly to tension pneumothorax and the ease with which pneumothorax can be treated if detected. As a result, CXRs are ordered as a precautionary measure for many patients that do not actually have pneumothorax. Further, because each patient with pneumothorax is typically subjected to multiple CXRs to generate subsequent films that document relative improvement, it is estimated that the total number of pneumothorax diagnostic tests conducted each year in the U.S. may be hundreds of thousands.

To overcome the diagnostic limitations of CXRs and CT, patients may be placed in the upright or lateral decubitus positions, and/or end-expiratory exposures may be used instead. Unfortunately, these positioning maneuvers are typically difficult to perform on critically ill patients. In addition to patient positioning difficulties, a common limitation of CXRs and CT is the difficulty and danger of transporting a critically ill patient to the imaging suite and the lack of equipment and staff availability in a timely manner, which is typically the case at night or in remote areas (such as, for example, battlefield conditions, the scene of an accident, a bedside, etc.). Further, CXRs, CT and other conventional imaging techniques typically involve a significant amount of delay between the examination of a patient and the availability of diagnostic results. Such a delay may be unacceptable in many situations, particularly where the patient's condition is critical or life-threatening. Still further, as is commonly known, diagnostic techniques based on ultrasound suffer from a high false positive rate due to inherent limitations.

Some researchers have used zero radiation techniques that rely on external low frequency forcing to non-invasively diagnose lung. diseases other than pneumothorax. For example, Wodicka et al. [Wodicka G R, Aguirre A, DeFrain P D, and Shannon D C, *Phase Delay of Pulmonary Acoustic Transmission from Trachea to Chest Wall*, IEEE Transactions on Biomedical Engineering 1992; 39:1053-1059] and Kraman et al. [Kraman S S, Bohandana A B, *Transmission to the Chest of Sound Introduced at the Mouth*, J Applied Physiology, 1989; 66:278-281] studied acoustic transmission characteristics from the trachea to the chest wall by introducing low frequency sound waves at the mouth and measuring the sound waves received at the chest wall. The Wodicka et al. study found that geometrical changes within the lung cause sound transmission times to be frequency dependent because different wavelengths of sound couple to different parts of the lung lining. The Kraman et al. study found that changes in the lung volume or the resident gas composition did not consistently alter the peak-to-peak amplitude or the peak frequency of the measured signal. On the other hand, Donnerberg et al. [Donnerberg R L, Druzgalski C K, Hamlin R L, Davis G L, Campbell R M, Rice D A. British J, *Diseases of the Chest* 1980;74: 23-31] studied the sound transfer function in normal and congested dog lungs using a technique similar to that described by Wodicka et al. and found a consistent increase in the transmitted sound as the lung wet-to-dry weight ratio increased.

Another abnormal respiratory condition that typically occurs in patients in ambulances and operating rooms is the misplacement of an endotracheal (ET) tube within a patient's trachea. As is generally known, ET tubes are placed in patients to establish an open airway, deliver anesthetic agents, and/or to perform mechanical ventilation. Typically, when an ET tube is misplaced, it travels too far into one of the two main bronchi (i.e., left and right) and blocks the other bronchus partially or completely, thereby limiting or eliminating ventilation into the lung associated with the obstructed bronchus. ET tube misplacement may also occur after the ET tube has been initially properly placed. For example, the ET tube may spontaneously move due to movements of the patient and/or movements of the ventilator tubing attached to the ET tube. Additionally, an ET tube may be misplaced into the esophagus of a patient or may be misplaced as a result of extubation.

As is well known, ET tube misplacement is a leading cause of hypoxemia and death during the course of general operative anesthesia, obstetric anesthesia, and in the management of critically ill patients in the intensive care unit, emergency room, and emergency settings outside the hospital environment. For example, mainstem intubation of a unilateral bronchus (i.e., placement of the ET tube into a left or right bronchus) may occur in approximately one-third of emergency endotracheal intubations because such emergency intubations depend heavily on operator skill and the clinical environment. Esophageal intubation and dislodgment of an endotracheal tube from its proper position or location are also relatively common occurrences. Unfortunately, ET tube misplacements are typically not recognized until after a chest radiograph is analyzed by a physician and, as a result, may lead to significant cerebral injury and/or death.

The most reliable known method of detecting proper endotracheal tube placement or location is direct visualization of the endotracheal tube passing through the vocal cords. However, under certain circumstances (e.g., blind nasal endotracheal intubation or endotracheal intubation through a laryngeal mask airway), such direct visualization may not be possible. Additionally, redundant soft tissue, blood, or the endotracheal tube itself may obscure a direct view of the vocal cords.

Due to the difficulty associated with detecting ET tube placement or location via direct visualization, ET tube placement or location is typically checked using x-rays, physiologic or acoustic techniques. However, the time, cost and radiation exposure associated with x-rays limits the usefulness of x-ray based detection of ET tube location, especially when multiple or on-line monitoring of the ET tube location is desired.

Physiologic techniques such as pulse oximetry and end-tidal $CO_2$ detection are commonly employed to detect endotracheal tube location. Specifically, detection of end-tidal $CO_2$ by capnography, capnometry, or colorimetric analysis may be used to detect ET tube location. However, with $CO_2$-based techniques detection results may be corrupted if the patient has ingested carbonated beverages or antacids or if pulmonary blood flow is diminished or absent during cardiopulmonary resuscitation. While various $CO_2$ detection techniques can be useful in detecting location of an ET tube, these techniques are typically not reliable for detection of mainstem bronchus ET tube malpositioning and provide limited accuracy.

Still further, some researchers such as, for example, Wodika et al. noted above, have used acoustic techniques to detect ET tube placement or location. The acoustic techniques described by Wodika et al. typically use an acoustic generator attached to one end of an ET tube to send sounds through the ET tube. Sounds reflected at a tip of the ET tube and sounds reflected by the airways within the patient are detected by acoustic sensors located near the acoustic generator. An analysis of the incident and reflected sounds may be used to facilitate ET tube positioning and monitoring.

SUMMARY OF THE INVENTION

A system and method for use in detecting an endotracheal tube location within a body may electronically detect indigenous breath sounds emanating from a region of the body and may process the detected indigenous breath sounds to generate a parameter representative of an acoustic characteristic of the body associated with the endotracheal tube location within the body. The system and method may also generate an output indicative of the endotracheal tube location within the body based on the parameter representative of the acoustic characteristic of the body.

In some embodiments, the system and method may electronically detect the indigenous breath sounds emanating from the region of the body by receiving an electrical signal from one or more acoustic sensors disposed adjacent to one of a chest region of the body and/or an epigastric region of the body. The system and method may process the detected indigenous breath sounds to generate the parameter representative of the acoustic characteristic of the body associated with the endotracheal tube location within the body by calculating a spectral energy ratio.

BRIEF DESCRIPTION OF THE DRAWINGS

FIGS. 6a-6f are exemplary graphical representations showing spectra of indigenous respiratory sounds for normal and pneumothorax states within six test subjects;

FIG. 7b is an exemplary graphical representation showing spectra of indigenous respiratory sounds for an abnormal respiratory condition in which an ET tube is located in the right bronchus of the test subject of FIG. 7a;

DESCRIPTION

A pneumothorax condition results in the presence of a gas cavity in the pleural space that separates the lung parenchyma and the chest wall. At frequencies below 10 kilohertz (kHz) sound wavelengths significantly exceed alveolar size and the lung parenchyma acts as a foam-like substance made of a mixture of air and soft tissue. At frequencies below 10 kHz, predominantly compression wave propagation is supported and because the composite density of the lung is dominated by the tissue component, the resulting speed of sound through the lung parenchyma is low (e.g., 25-70 meters per second (m/s)), which is much lower than the speed of sound in free air and soft tissue (i.e., 330 m/s and 1500 m/s, respectively). This large difference in sound speed and in mass density (of air compared to tissue) combine to create a relatively large acoustic impedance mismatch between the lung tissue and the gas cavity. Thus, when sound waves introduced at a patient's mouth travel through the airways and the lung parenchyma to the chest wall, this impedance mismatch causes a large decrease (typically 20-30 dB) in the amplitude (i.e., attenuation) of the sound waves received at the chest wall.

Figure 1:
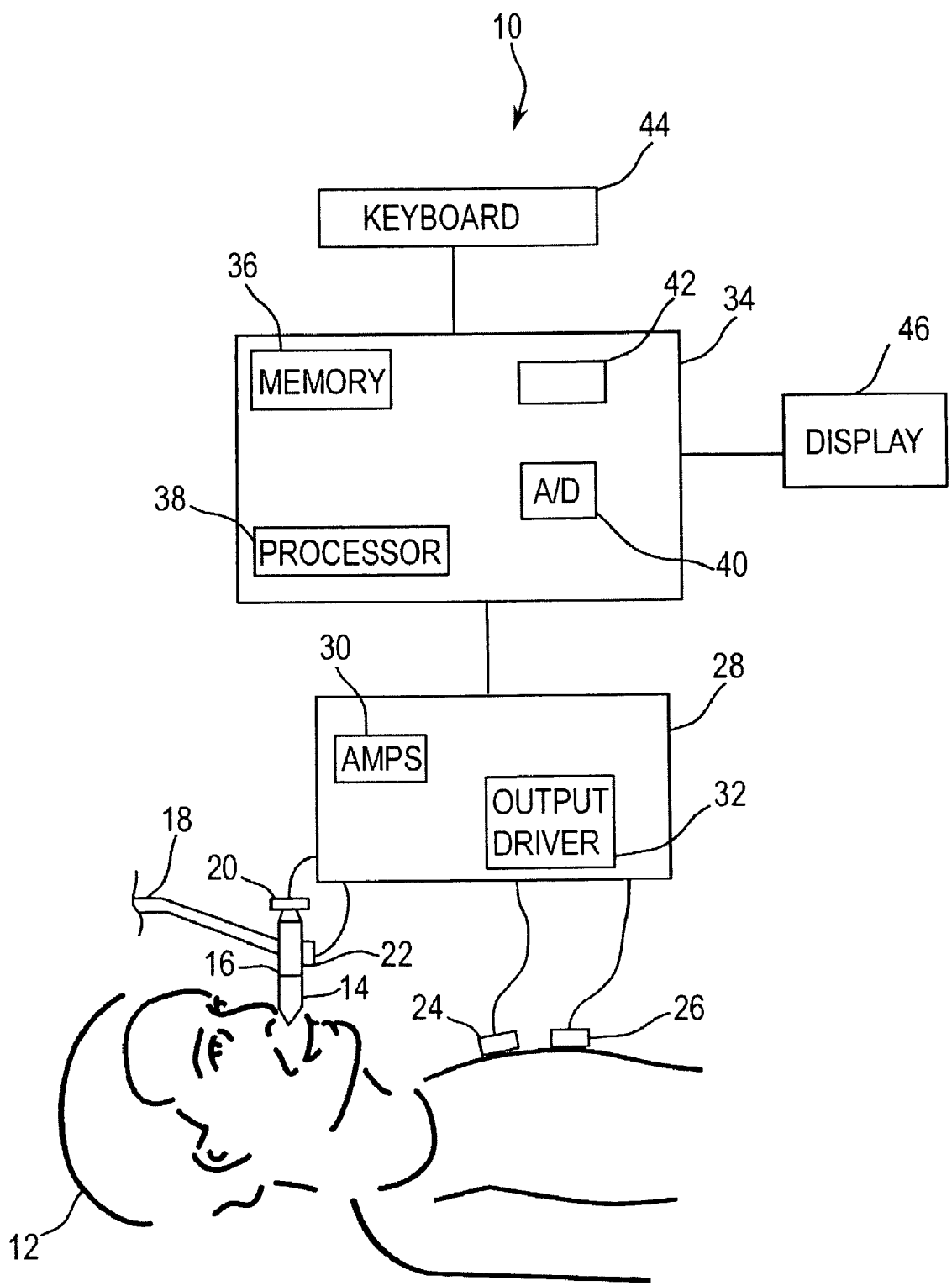
FIG. 1 is an exemplary schematic block diagram illustrating a system for measuring the acoustic response characteristics from the mouth to the chest wall of an endotracheally intubated patient.
Figure 2:
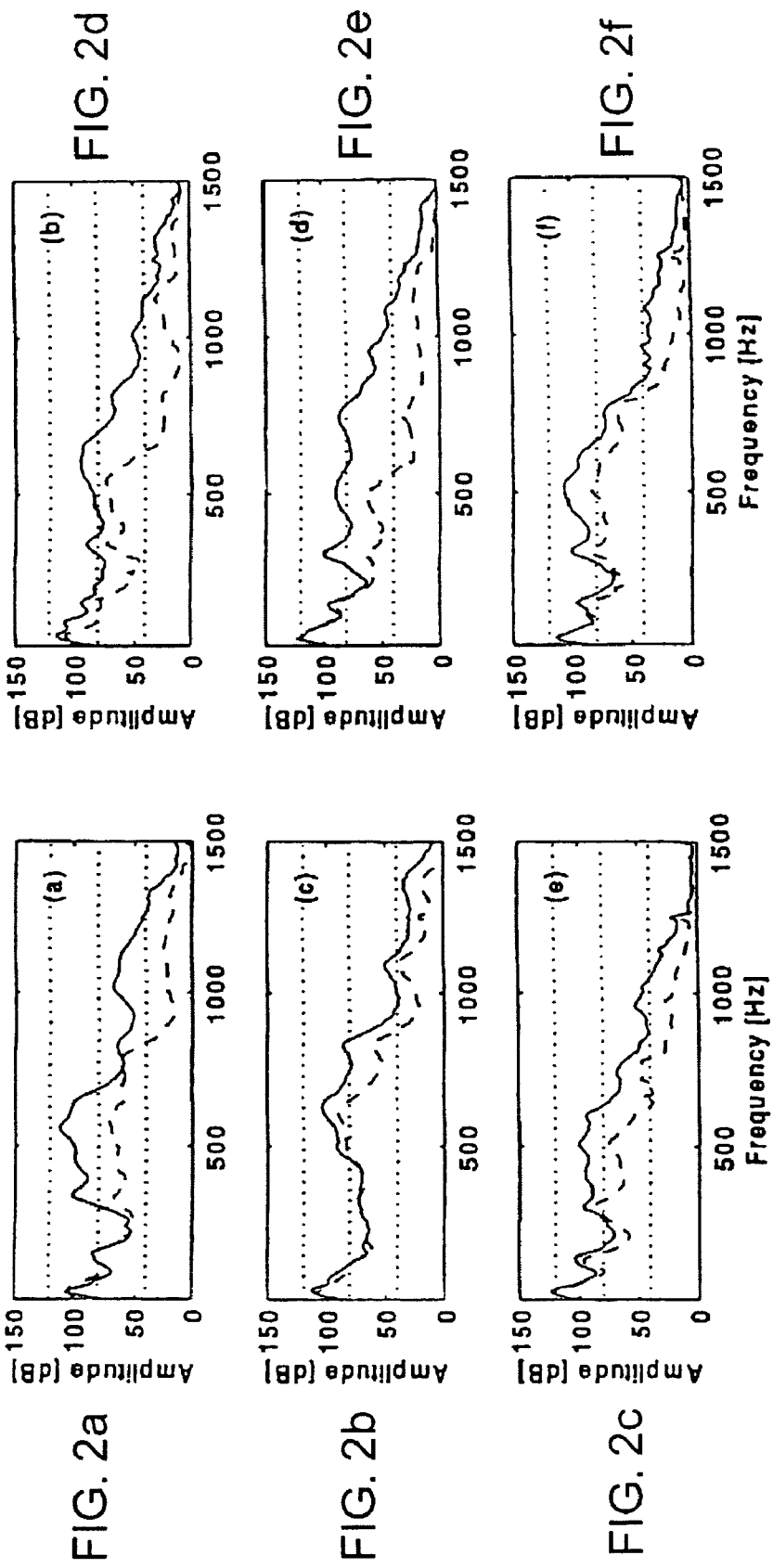
FIGS. 2a-2f are exemplary graphical representations of the acoustic response characteristics of six test subjects measured from their mouths to their chest walls.

FIG. 1 is an exemplary schematic block diagram illustrating a system 10 for measuring the acoustic response characteristics from the mouth to the chest wall of an endotracheally intubated patient 12. As shown in FIG. 1, an endotracheal (ET) tube 14 is inserted into the mouth and trachea of the patient 12 in a conventional manner. A "T" shaped tube 16 (hereinafter referred to as a "T-tube") is axially aligned with and is coupled to the ET tube 14 to enable a ventilator output tube 18 to provide a supply of air to the patient 12. A speaker 20, or any other suitable actuator, may be coupled to the T-tube 16 and may be driven to produce sound waves, which may or may not be in the audible range (i.e., 20 Hz-20 kHz), that are conducted by the T-tube 16 and the ET tube 14 into the mouth and trachea of the patient 12. Additionally, a microphone 22, or any other suitable sensor that detects acoustic vibrations, is coupled to the T-tube 16 so that the sounds produced by the speaker 20 can be monitored and/or so that sounds emanating from the trachea of the patient 12 can be detected, if desired.

Surface sensors 24 and 26 are adjacent to, and preferably in contact with, the chest of the patient 12 and are configured to detect and measure sound waves impinging on the chest wall of the patient 12. The surface sensors 24 and 26 may be electronic stethoscopes, air-coupled microphones, accelerometers, contact microphones, capacitive or optical vibration sensors, or any other transducer that converts vibrations or sound waves into electrical signals.

The surface sensors 24 and 26, the microphone 22, and the speaker 20 are electrically coupled to a signal conditioning unit 28 that includes amplifiers 30 and an output driver 32. The amplifiers 30 receive low-level signals from the microphone 22 and one or more of the surface sensors 24 and 26 and convert these low-level signals into high-level signals, which are coupled to a processing unit 34. The output driver 32 receives and converts low power signals from the processing unit 34 into signals that are suitable for driving the speaker 20, which is typically a low impedance device having an inductive load characteristic.

The processing unit 34 includes a memory 36, a processor 38, an analog-to-digital converter (A/D) 40 and a plurality of software routines 42 that may be stored on the memory 36 and executed by the processor 38 to perform the diagnostic techniques described herein. The processing unit 34 may be based on a variety of commercially available platforms such as a personal computer or a workstation, or may be based on a custom platform that uses application-specific integrated circuits (ASICs) and other custom circuitry to carry out the diagnostic techniques described herein. Additionally, the processing unit 34 is coupled to one or more input/output (I/O) devices that enable a user to interface to the system 10. By way of example only, the processing unit 34 may receive user inputs via a keyboard 44 or any other data input device and may provide graphical displays to the user via an output device or display unit 46, which may be, for example, a conventional video monitor, incandescent lights, light-emitting diodes, liquid crystal displays, etc., any combination of which may function as simple two state indicators, textual and/or numerical information, etc. In addition, the display unit 46 may be adapted to generate audible alarms and/or other audible information.

In operation, the system 10 shown in FIG. 1 is controlled by the processing unit 34 to respond to user inputs, which, for example, may cause the processing unit 34 to begin execution of one or more of the software routines 42, thereby enabling the user to acoustically detect a respiratory condition within the patient 12. By way of example only, the processing unit 34 may execute one of the software routines 42 that provides a signal to the output driver 32 of the signal conditioning unit 28, which in turn drives the speaker 20 to produce sound waves. These sound waves may, for example, include frequency components of uniform amplitude over a 20 Hz to 1600 Hz range. However, sound waves including other frequency ranges and having different amplitude characteristics may be used without departing from the scope and the spirit of the invention.

In any event, the sound waves generated by the speaker 20 travel through the T-tube 16, the ET tube 14 and into the mouth and trachea of the patient 12. Alternatively, in the case of a non-intubated patient, the sound waves generated by the speaker 20 may be directed into the mouth of the patient using a mask and/or a mouthpiece rather than the ET tube 14. If a mask and/or mouthpiece is used to direct the sounds waves into the patient's mouth, a nasal clip may also be used to encourage oral airway patency. However, in the case where the patient is unconscious, an oral airway may be used instead. In any event, the sound waves then travel through the trachea and lungs and impinge on the chest wall of the patient 12.

The microphone 22 is responsive to the input sound waves generated by the speaker 20 and generates electrical signals representative of these input sound waves that are coupled to the amplifiers 30. In a similar manner, the surface sensors 24 and 26 are responsive to the vibrations imparted to the chest wall of the patient 12 by the sound waves and generate electrical signals representative of these chest wall vibrations that are coupled to the amplifiers 30. The electrical signals representative of the input sound waves and the chest wall vibrations are amplified by the amplifiers 30 and the amplified signals are coupled to the processing unit 34 which, as described in greater detail below, processes the amplified signals to enable a user to detect a respiratory condition within the patient 12.

The amplified signals associated with the input sound waves and the chest wall vibrations are converted into respective streams of digital data by the A/D 40 and these digital data streams are converted by the processor 38 into respective frequency domain representations (i.e., spectra) using a fast Fourier transform (FFT) or any other data processing technique that produces spectral information or data from digitized time domain waveforms. The spectrum associated with the input sound waves and the spectra associated with the chest wall vibrations can then be used to determine the transfer function of the patient's mouth, trachea, lungs and chest which, as described below, may include indicators of an abnormal respiratory condition within the patient 12. Additionally, the time domain waveforms associated with the input sound waves and the chest wall vibrations can be compared to one another to measure coherence and time delays between the input sound waves and the chest wall vibrations, which may be indicative of an abnormal respiratory condition. Although two surface sensors are shown in the system 10 of FIG. 1, it is important to recognize that one, three or any other number of surface sensors may be used instead to carry out the diagnostic techniques described herein without departing from the scope and the spirit of the invention.

FIGS. 2*a*-2*f* are exemplary graphical representations of the acoustic response characteristics of six test subjects (i.e., transfer functions) measured from their mouths to their chest walls using the system shown in FIG. 1. The solid lines shown in these graphs represent the acoustic response characteristics for a normal respiratory condition within each of the test subjects and the dashed lines represent the acoustic response characteristics for a pneumothorax condition within each of the test subjects. As can be seen in these graphs, the pneumothorax condition is characterized by a substantial attenuation of the sound waves having a frequency greater than about 300 Hz. In contrast, the sound waves having a frequency in the range of about 0 Hz to 250 Hz appear to be relatively unaffected by the pneumothorax condition.

Figure 3:
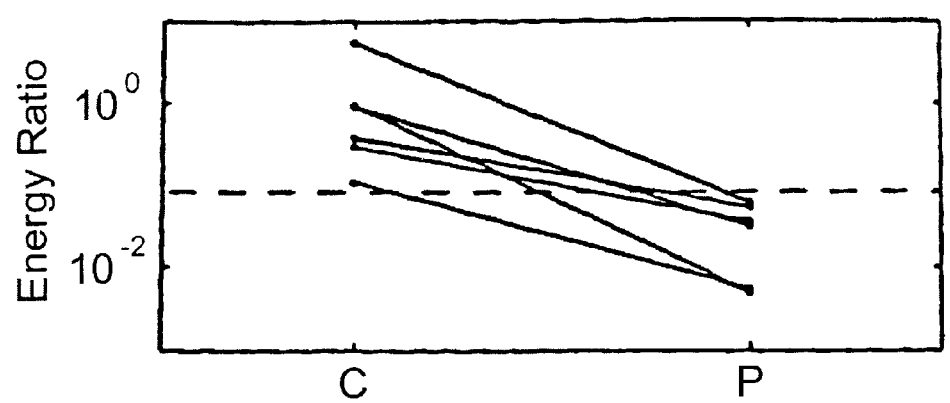
FIG. 3 is an exemplary graphical representation showing the ratios between the acoustic energies of a high frequency band of sound waves and a low frequency band of sound waves transmitted from the mouth to the chest wall within each of six test subjects using the system shown in FIG. 1.

FIG. 3 is an exemplary graphical representation showing the ratios between the acoustic energies of a high frequency band of sound waves and a low frequency band of sound waves transmitted from the mouth to the chest wall within each of six test subjects. For the measurements shown in FIG. 3, the high frequency band was defined as 550 Hz to 780 Hz and the low frequency band was defined as 8 Hz to 224 Hz. According to the test results shown in FIG. 2, the energy ratio (i.e., the energy associated with the high frequency band divided by the energy associated with low frequency band) decreases substantially when a pneumothorax condition is present. FIG. 3 shows the energy ratios calculated for both normal respiratory conditions, which are denoted as "C" on the horizontal axis, and pneumothorax conditions, which are denoted as "P" on the horizontal axis. As can be seen in FIG. 3, the energy ratio in all cases exceeded 0.10 for normal respiratory conditions and, in all cases, fell below 0.06 for abnormal respiratory conditions due to pneumothorax. Thus, a threshold value of 0.08 may be used to completely separate a normal respiratory condition from an abnormal pneumothorax condition so that if an energy ratio of less than 0.08 is calculated by the system 10, the system 10 can reasonably indicate to the user (e.g., a physician) that a pneumothorax condition is probably present.

Figure 4:
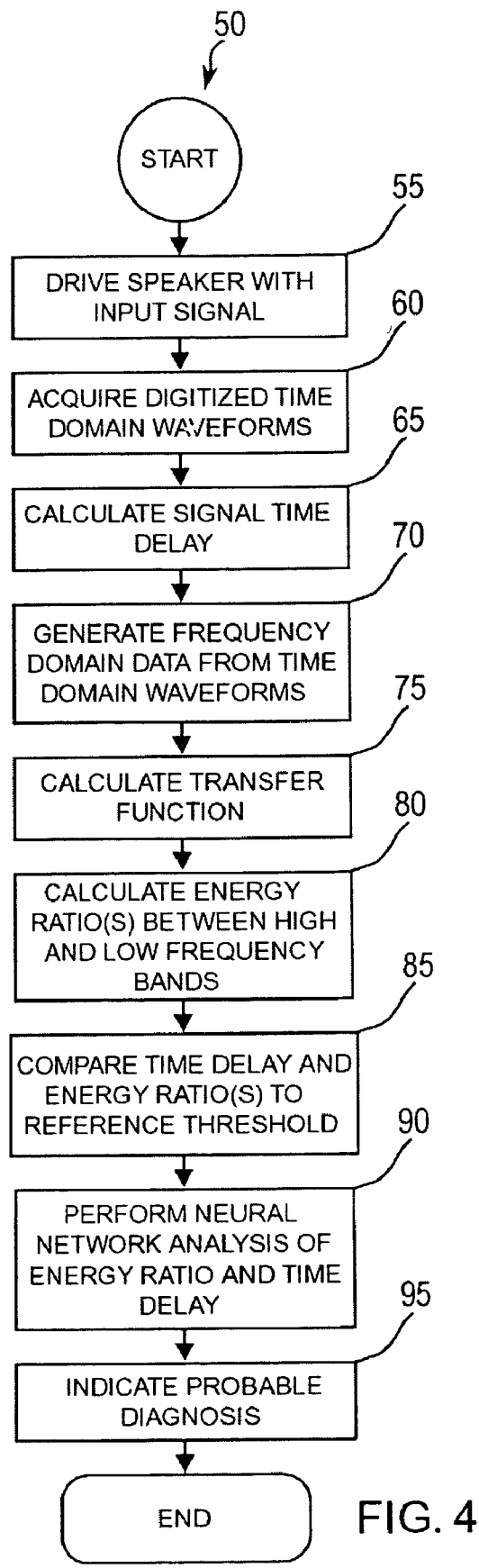
FIG. 4 is a flow diagram representing one method by which the acoustic response characteristics of a patient's chest and lungs may be analyzed using the system shown in FIG. 1.

FIG. 4 is a flow diagram representing one method 50 by which the acoustic response characteristics of a patient's chest and lungs may be analyzed using the system shown in FIG. 1. In a first block 55, the processing unit 34 sends input signals to the signal conditioning unit 28 that are amplified by the output driver 32 and coupled to the speaker 20. Preferably, but not necessarily, the amplified input signals cause the speaker 20 to produce sound waves having a broadband noise characteristic. For example, the speaker 20 may generate sound waves having relatively constant amplitude over a frequency range of 20 Hz to 1600 Hz. Of course, other frequency ranges and amplitude characteristics could be used as well without departing from the scope of the invention. For example, a click signal, a chirp signal, swept frequency signal or a signal containing a single frequency or a selected band of frequencies could be used instead of a broadband noise signal.

In block 60, the processing unit 34 acquires digitized time domain waveforms associated with inputs received from the microphone 22 and one or more of the surface sensors 24 and 26. As will be discussed in greater detail below, depending on the particular respiratory condition that the user desires to detect, the signals from one or more of the surface sensors 24 and 26 may be acquired by the processing unit 34. Additionally, the precise location of the surface sensors 24 and 26 on the chest of the patient 12 may be varied to optimize detection of a particular respiratory condition. For example, to detect a pneumothorax condition, the surface sensors 24 and 26 may be located at the clavicle lines at about the level of the third rib (on the left and right sides) of the patient 12. Further, in block 60, the processing unit 34 stores the digitized waveforms in the memory 36 for subsequent processing.

In block 65, the processing unit 34 calculates an input signal transmission time delay by comparing the acquired time domain signal associated with the microphone 22 to the acquired time domain signals associated with the surface sensors 24 and 26. The transmission time delay represents the amount of time it takes for sound waves to travel from the mouth of the patient 12 to the locations on the chest wall of the patient 12 that are adjacent to the surface sensors 24 and 26.

In block 70, the processing unit 34 generates frequency domain data from the acquired time domain signals. In other words, the processing unit 34 generates spectra representative of the input sound waves and chest wall vibrations. In block 75, the processing unit 34 uses the spectral data generated in block 70 to calculate the transfer function from the patient's mouth to the chest wall as the quotient of the cross spectrum of the input sound waves and the chest wall vibrations and the power spectrum of the input sound waves.

In block 80, the processing unit 34 calculates an energy ratio (or ratios if signals from both of the surface sensors 24 and 26 are used) by determining the total acoustic energy in a high frequency band, which may, for example, be 550 Hz to 780 Hz, and the total acoustic energy in a low frequency band, which may, for example, be 8 Hz to 224 Hz, and then dividing the total energy for the high frequency band by the total energy calculated for the low frequency band. These total energy calculations may, for example, be made by adding the transfer function values for all of the frequency bins (i.e., the discrete frequencies associated with FFT results) within each frequency band. Further, the spectral ranges associated with the upper and lower frequency bands may be optimized to enable the detection of particular respiratory conditions.

In block 85, the processing unit 34 compares the time delay calculated in block 65 to a predetermined time delay threshold value and compares the energy ratios calculated in block 80 to a predetermined energy ratio threshold, which may, for example, be 0.08 as discussed above. In block 90, the processing unit 34 performs a neural network analysis of the time delay value from block 65 and the energy ratio value from block 80. As is commonly known, neural networks are essentially one or more software routines that are responsive to input parameters based on a set of training data, which condition the behavior of the network. For example, a set of training data containing energy ratios and time delay values associated with known respiratory conditions could be used to train the neural network routines. The neural network routines may, for example, generate a diagnostic indicator value, which may range from zero to one and which is indicative of a possible diagnosis. The value "1" may represent a healthy patient and the value "0" may represent a particular abnormal respiratory condition, and values between zero and one may represent the degree to which a patient's condition corresponds to either the healthy condition or the abnormal respiratory condition. In operation, the trained neural network routines receive calculated time delay values and energy ratio values and use these values to generate a diagnostic indicator value ranging from zero to one.

In block 95, the processing unit 34 may use one or more of the comparisons of the time delays and the energy ratios to the respective time delay and/or energy ratio thresholds and/or may also use the output of the neural network analysis (i.e., the diagnostic indicator), or any other suitable output classification scheme, to indicate a probable diagnosis to the user. For example, if the result of the comparison of the energy ratio to the energy ratio reference threshold in block 85 is that the energy ratio exceeds the energy ratio reference threshold and/or, if the time delay falls outside of an allowable range of time delays, the processing unit 34 may indicate (via a textual and/or graphical display within the display 46) in block 95 that an abnormal respiratory condition, such as pneumothorax, is present. Alternatively or additionally, if the neural network analysis in block 90 produces a diagnostic indicator value which is sufficiently close to zero (or is below some threshold associated with a normal healthy condition), then the processing unit 34 in block 95 may indicate that an abnormal respiratory condition, such as pneumothorax, is present. Still further, the probable diagnosis determined in block 95 may be a result of any combination of comparisons made in block 85 and the neural network analysis of block 90. In fact, it may be desirable in some applications to require use of more than one of these comparisons and/or the neural network analysis to achieve a higher confidence in the probable diagnosis determined in block 95.

Figure 5:
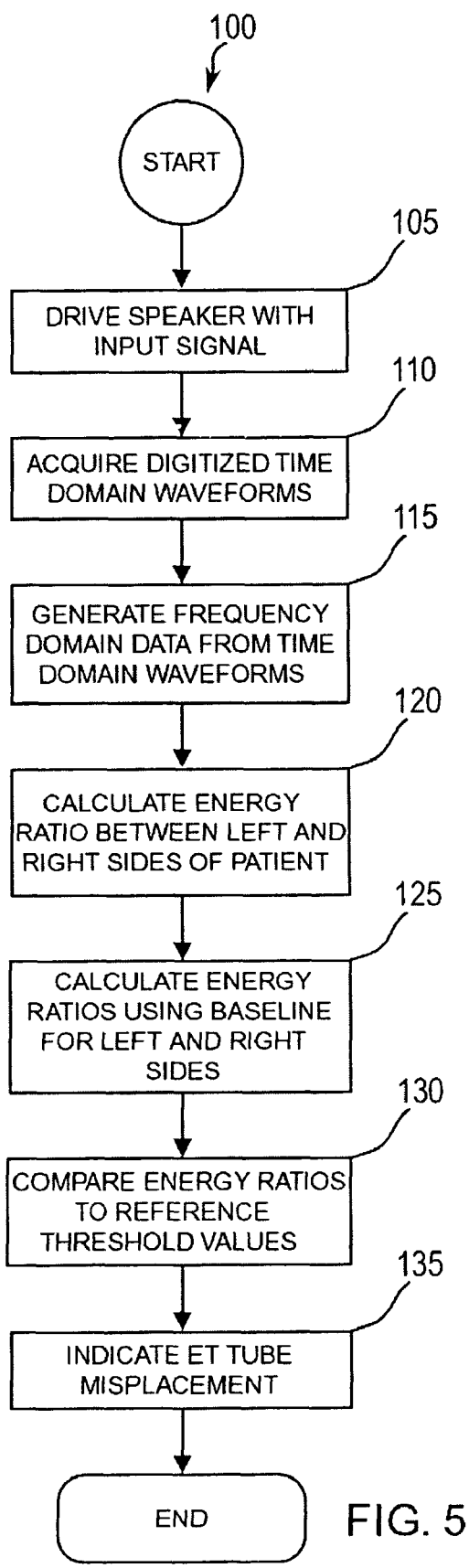
FIG. 5 is a flow diagram representing another method by which the acoustic response characteristics of a patient's chest and lungs may be measured using the system shown in FIG. 1.

FIG. 5 is a flow diagram representing another method 100 by which the acoustic response characteristics of a patient's chest and lungs may be measured using the system of FIG. 1. As discussed in greater detail below, the method 100 may be used to determine whether an ET tube has been properly located within a patient's trachea. More specifically, the method 100 enables a user (e.g., a physician) to determine on a real time basis whether an ET tube has been misplaced such that the one of the patient's bronchi is partially or completely blocked, thereby creating an abnormal respiratory condition within the patient 12 (FIG. 1). Typically, to detect ET tube placement or location, the surface sensors 24 and 26 are located so that one of the surface sensors 24 and 26 is adjacent to the left side of the patient's chest and the other one of the sensors 24 and 26 is located adjacent to the right side of the patient's chest.

In block 105, the processing unit 34 (FIG. 1) sends input signals to the signal conditioning unit 28 that cause the speaker 20 to produce sound waves having a broadband noise characteristic and, in block 110, the processing unit 34 acquires digitized time domain waveforms associated with inputs received from one or more of the surface sensors 24 and 26. To detect an abnormal respiratory condition such as ET tube misplacement within a patient's trachea, the time domain waveforms acquired in block 110 may be acquired multiple times. For example, time domain waveforms may be acquired before the ET tube 14 has been inserted into the patient 12 to establish baseline acoustic characteristics. Additional time domain waveforms may then be acquired repeatedly as the ET tube 14 is inserted and, as described in greater detail below, the acoustic characteristics derived from these additional time domain waveforms may be compared to one another and to the initial baseline characteristics to determine whether the ET tube 14 is positioned improperly.

In block 115, the processing unit 34 generates frequency domain data (i.e., spectral data) from each of the time domain waveforms acquired in block 110 and stores this frequency data in the memory 36. In block 120, the processing unit 34 calculates an energy ratio between the left and right sides of the patient 12 by dividing the total energy within a frequency band of the frequency domain data associated with one of the surface sensors 24 and 26 by the total energy within a corresponding frequency band of the frequency domain data associated with the other one of the surface sensors 24 and 26. Thus, in block 120, the processing unit 34 calculates a value that is indicative of a relative comparison between the intensity of the vibrations or sound waves received by the surface sensors 24 and 26 within a particular frequency band. While the method 100 of FIG. 5 is described by way of example to use a single frequency band to calculate energy ratios, additional frequency bands could alternatively be used to calculate the one or more energy ratios without departing from the scope of the invention.

In block 125, the processing unit 34 calculates energy ratios by dividing the energies within a particular frequency band (or bands) by respective baseline energies within that band (or bands) that are established prior to insertion of the ET tube 14. In block 130, the processing unit 34 compares the energy ratios calculated in blocks 120 and 125 to a set of reference threshold values and, in block 135, the processing unit uses the results of the comparisons made in block 130 to indicate whether or not the ET tube 14 is properly positioned within the patient's trachea. When an ET tube is misplaced, it typically migrates into one of the main bronchi, which results in sound waves being attenuated more on the side associated with the obstructed bronchus as compared to the other (i.e., unobstructed) side of the patient 12 and also results in the sound waves or vibrations measured on the obstructed side being attenuated with respect to the baseline measurements of that side. In block 135, the processing unit 34 indicates that the ET tube 14 has been misplaced (i.e., has migrated into one of the main bronchi) when the energy ratio between the left and right side measurements crosses a predetermined threshold value, which may be adjusted by the user to control the sensitivity of the system 10. Alternatively or additionally, the processing unit 34 may use the results of the comparisons of the energy ratios based on the left and right side measurements and the respective baseline left and right side measurements to determine whether the ET tube 14 has been misplaced.

The system 10 shown in FIG. 1 may also be used to detect respiratory conditions without using any input of sound waves to the patient's mouth and trachea. Instead, one or more of the surface sensors 24 and 26 may be used to analyze indigenous respiratory sounds to assess the respiratory conditions within the patient 12.

Respiratory sounds are routinely used for clinical assessment of respiratory function and the characteristics of normal and some abnormal respiratory sounds have been extensively studied. The normal respiratory sound spectrum is known to peak below 100 Hz where the signal is mixed with muscle and cardiovascular sounds. Above 100 Hz, the signal amplitude drops sharply but is still measurable up to about 1000 Hz [Pasterkamp et al. 96]. Higher frequencies are more pronounced in smaller subjects, which is usually attributed to less transmission attenuation in their smaller lungs and thinner chest walls. The sound amplitude is known to be proportional to the square of the airflow, to increase toward the lung bases posteriorly and to decrease toward the bases anteriorly. These sounds depend on respiratory cycle timing because of intra-cyclic airflow variability. Furthermore, the reversal in airflow directionality during inspiration compared to expiration alters sound generation in different lung regions secondary to flow turbulence changes.

As is commonly known, pneumothorax results in diminished breath sounds during physical examination. Other conditions that can lead to faint lung sounds include stenosis of the main, intermediate, or lobar bronchi, which can be detected over the parts of the lung supplied by the affected airway, whereas vocalizations tend to be unchanged at these locations. Some studies have also correlated poor ventilation with diminished lung sounds below 300 Hz, which may overlap with the pneumothorax acoustic signature.

FIGS. 6a-6f are exemplary graphical representations showing spectra of indigenous respiratory sounds for normal and pneumothorax states within six test subjects. Each spectrum shown in FIGS. 6a-6f contains more than twelve respiratory cycles for each of the six test subjects. Using a FFT, the spectral content of the respiratory sounds was calculated for each 1024-point data segment after windowing with a Hanning window, which resulted in a frequency resolution of 8 Hz. Data segments overlapped by 50% and the mean spectral values were determined by averaging results from all segments. Tracking the respiratory cycle with a separate sensor, or with a contact sensor as described above, enables respiratory sound analysis at different points within the respiratory cycle. This type of gated analysis helps to optimize the performance of the system 10.

As shown in FIGS. 6a-6f, at frequencies below 30 Hz the amplitude of respiratory sounds within each test subject decreases with decreasing frequency due to the inherent high pass cut off (at 20 Hz) of the acoustic sensors or electronic stethoscopes used for the surface sensors 24 and 26. Signal amplitudes of the normal respiratory condition and the abnormal pneumothorax condition were not significantly different below 100 Hz to 200 Hz. In fact, the amplitude attenuated at 21.8+−2.9 dB/Octave (mean+−standard deviation) with increasing frequency in the 30 Hz to 200 Hz range under both normal respiratory conditions and abnormal respiratory conditions. This drop in amplitude may be due to an increase in sound transmission resistance and a decrease in sound generation.

Amplitude changes as a result of pneumothorax were most pronounced in the 300 Hz to 500 Hz range. This difference likely results from the large impedance mismatch that occurs when the lung pulls away from the inner chest wall forming an air gap or gas cavity and also results from decreased sound generation in the respiratory system as a result of decreased airflow and turbulence.

In any event, as suggested by the spectral graphs shown in FIGS. 6a-6f, the method 50 shown in FIG. 4 may be used to analyze indigenous respiratory sounds to detect abnormal respiratory conditions. However, in using the method 50 of FIG. 4, the block 55, which drives the speaker 20 to cause sound waves to enter the patient's mouth, is omitted, and any signal time delay calculations or use of time delay values are similarly omitted. Additionally, in adapting the method 50 of FIG. 4 for use in analyzing indigenous respiratory sounds, the frequency bands used to calculate the energy ratios may be optimized to maximize the confidence in the diagnostic output in block 95.

Because respiratory sounds are primarily a result of airflow-induced turbulence, the method 100 shown in FIG. 5 (less block 105) may also be used to analyze indigenous respiratory sounds to detect an abnormal respiratory condition such as a misplaced ET tube. When the ET tube is misplaced, ventilation is reduced in one of the lungs, which results in a decrease in the intensity of the respiratory sounds detected at the chest surface adjacent to the obstructed lung. In addition, the increase in airflow to the unobstructed lung causes an increase in the intensity of the respiratory sounds at the chest surface adjacent to the unobstructed lung, which further increases the sensitivity of the system 10 to a misplaced ET tube.

Further, because attenuation of acoustic waves within the respiratory system typically increases with frequency (i.e., higher frequencies are more heavily damped), the higher frequency components of indigenous respiratory sounds are more easily detected close to their point of origin. Thus, if an ET tube is misplaced and extends into the one of the main bronchi, then the intensity of the high frequency components of the indigenous respiratory sounds generated by the under ventilated (i.e., obstructed) lung will decrease.

Figure 7B:
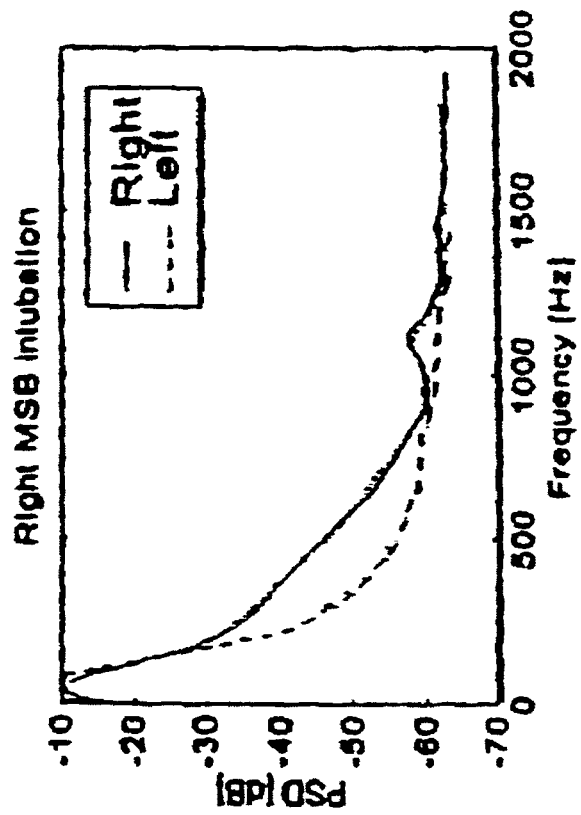
Figure 7A:
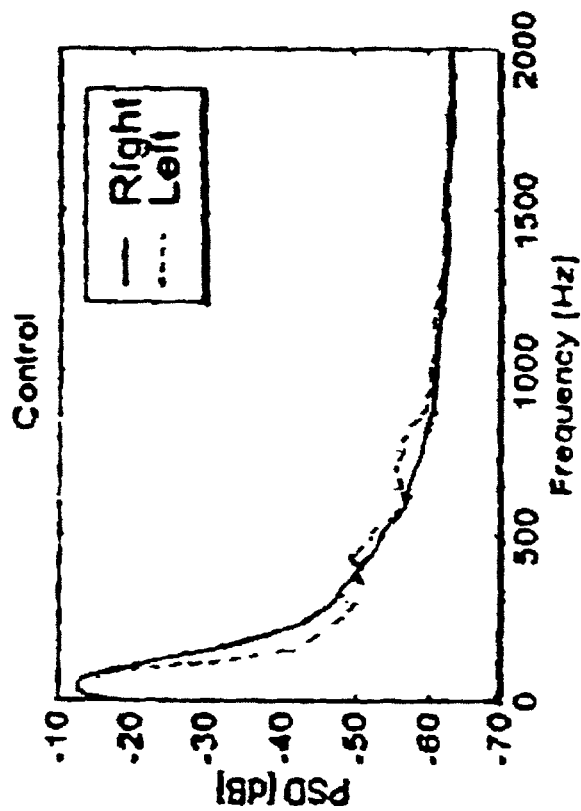
FIG. 7a is an exemplary graphical representation showing spectra of indigenous respiratory sounds for a normal respiratory condition within a typical test subject.

FIG. 7a is an exemplary graphical representation showing spectra of indigenous respiratory sounds for a normal respiratory condition within a typical test subject, and FIG. 7b is an exemplary graphical representation showing spectra of indigenous respiratory sounds for an abnormal respiratory condition in which an ET tube is located in the right bronchus of the test subject of FIG. 7a. As can be seen in FIGS. 7a and 7b, there is a general trend for increased attenuation with increasing frequency over the 50 Hz to 1500 Hz range. However, as shown in FIG. 7b, the over-advancement of the ET tube into the right bronchus results in a significant attenuation in the intensity of indigenous respiratory sounds within the left lung over the 200 Hz to 1200 Hz range. A maximum attenuation of indigenous respiratory sounds of about 15-20 dB was observed at about 400 Hz in the left lung.

Still further, if the ET tube is misplaced into the esophagus, ventilator air is forced into the stomach, which results in relatively loud epigastric sounds. Due to the substantial anatomic differences between the respiratory and upper gastrointestinal systems, sounds resulting from esophageal ventilation have spectral and temporal characteristics that are substantially different from normal condition respiratory sounds. For example, ventilation of the upper gastrointestinal tract exhibits a minimal expiratory phase, at least until enough air accumulates to cause a significant back pressure.

Still further, acoustic changes resulting from extubation depend primarily on the new ET tube position. Typically, pharyngeal positioning of the ET tube generates some transmitted acoustic energy to the chest wall. However, attenuation of higher frequencies and the amplitude of bilateral respiratory sounds also occurs.

Figure 8:
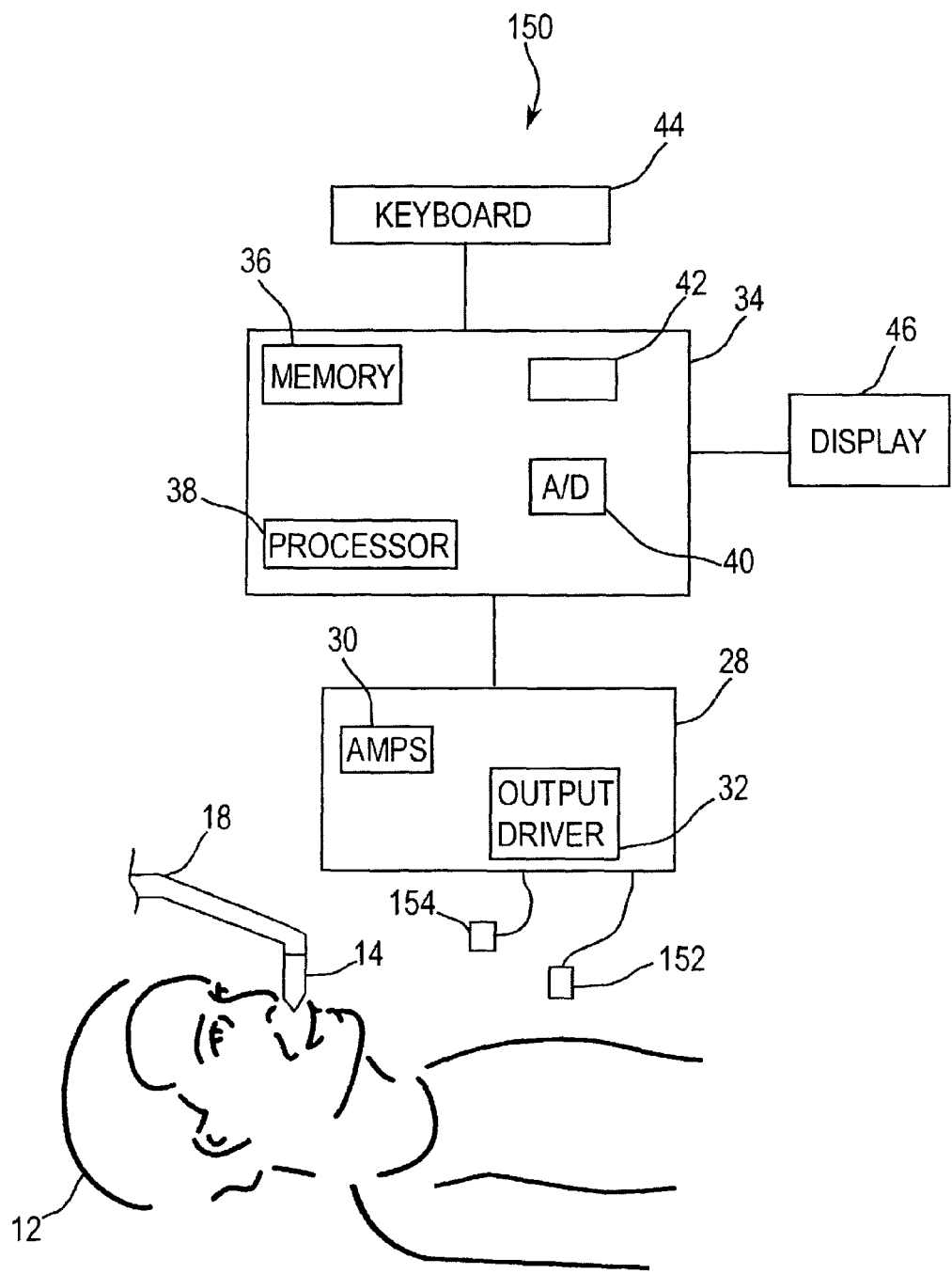
FIG. 8 is an exemplary schematic block diagram of an alternative system that uses percussive inputs to measure the acoustic response characteristics within the chest and lungs of an endotracheally intubated patient.

FIG. 8 is an exemplary schematic block diagram of an alternative system 150 that uses percussive inputs to measure the acoustic response characteristics of an endotracheally intubated patient's chest and lungs. Elements of the system 150 that are similar or the same as those of the system 10 shown in FIG. 1 are identified using the same reference numerals. However, in the alternative system 150 of FIG. 8, an impact hammer 152 and an air-coupled microphone 154 have been added to enable the detection of respiratory conditions within the patient 12 using percussive inputs to the patient's chest.

The alternative system 150 uses the impact hammer 152 to apply percussive inputs to the chest of the patient 12. The impact hammer 152 may be any suitable actuation device that imparts vibrations to the chest of the patient 12. Further, the hammer 152 may be manually activated by a user (e.g., a physician, technician, etc.) or may be activated automatically in the case where the hammer 152 is electrically powered such as, for example, where the hammer 152 is actuated by a solenoid. The hammer 152 may contact the chest of the patient 12 directly or, alternatively, may impact an anvil that interposes between the chest surface and the hammer 152.

The air-coupled microphone 154 is responsive to the sounds that emanate from the patient's chest following a percussive input by the hammer 152 and sends electrical signals representative of these sounds to the signal conditioning unit 28. The signal conditioning unit 28 uses the amplifiers 30 to amplify these electrical signals and couples the amplified signals to the processing unit 34 for further processing.

Figure 9:
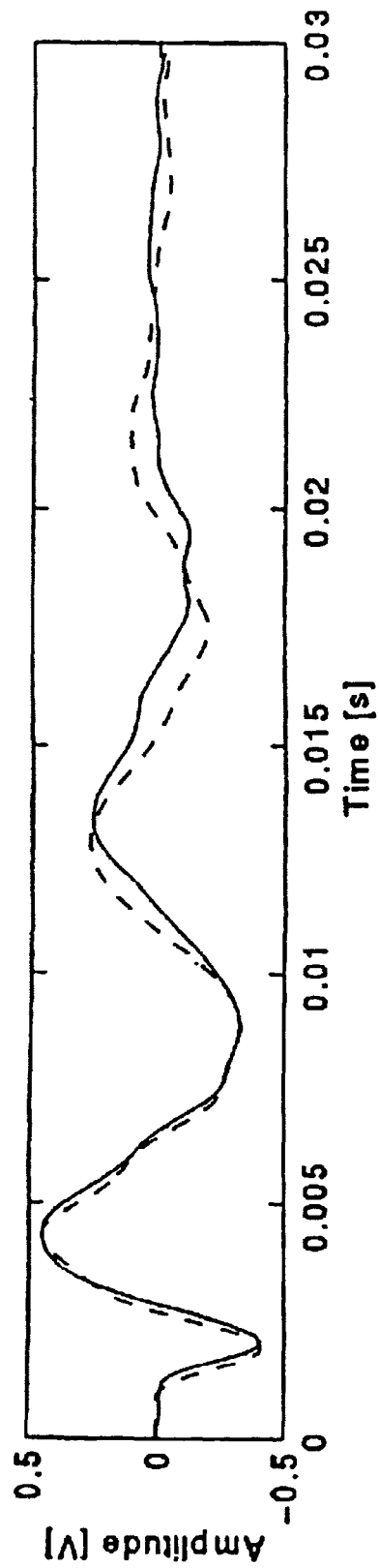
FIG. 9 is an exemplary graphical representation showing a typical acoustic chest response to a percussive input for a normal respiratory condition and a pneumothorax condition.

FIG. 9 is an exemplary graphical representation showing a typical acoustic chest response to a percussive input for a normal respiratory condition (solid line) and a pneumothorax condition (dashed line). In developing the graph shown in FIG. 9, percussion was introduced in seven dogs at the right mid-clavicular line by activating the impact hammer 152 to cause it to strike a stainless steel circular bar held against the chest wall parallel to the ribs in the third intercostal space. Percussion tests were performed for both normal respiratory conditions and a pneumothorax condition. During each test, fifteen percussive inputs were performed and the chest response was measured using the air-coupled microphone 154 placed a small distance away from the skin. The amplitude, dominant frequency, and decay rate were calculated for each input.

As shown in FIG. 9, each of the signals representative of the normal and pneumothorax conditions are about 20-30 ms in duration and show an initial spike followed by a decaying oscillatory signal with a narrow-band spectral content, which is typical of underdamped vibrating systems. However, it is clear from the percussive test results that the damped oscillatory response associated with a pneumothorax condition has a slower decay rate and also has a higher frequency than that of a normal respiratory condition.

The slower decay rate and the higher frequency associated with a pneumothorax condition may be a result of the tendency of the chest wall to vibrate at its natural frequency in response to percussive inputs and the fact that vibrations decay in time as a result of viscous dissipation of vibratory mechanical energy in the chest wall and lungs. Specifically, when pneumothorax is present, the lung pulls away from the chest wall and produces less damping, which results in a lower decay rate. In addition, as the underlying parenchyma is replaced by air, the vibrating mass of the system is lowered, which increases the resonant frequency of the system. These effects are consistent with what has been noted by skilled physicians as "hyperresonance" during physical examination.

Quantitative analysis of the above-noted percussive signals was performed to determine their decay rate and dominant frequency. To calculate the decay rate, the signal envelope was first determined as the instantaneous amplitude of the signal, followed by finding the best fit of the decaying portion of the envelope using regression analysis. The slope of the fitted curve then gave the decay rate. Both linear and exponential decay calculations were attempted. The dominant frequency was estimated from both zero-crossing and FFT algorithms. Zero-crossing provided a finer resolution (1-5 Hz in the 80-200 Hz range) as the FFT estimate was limited to 40 Hz due to the short duration of the signals. Wavelets and autoregressive analysis including the maximum entropy method were also performed.

Because of the large intersubject variability suggested by the data, parameter values of the control state (e.g., from the contralateral side or an initial baseline value at the same side) may be needed for accurate diagnosis. The large intersubject variability may be the reason for the conflicting reports about the sensitivity and specificity of manual percussion for the diagnosis of lung diseases.

Figure 10:
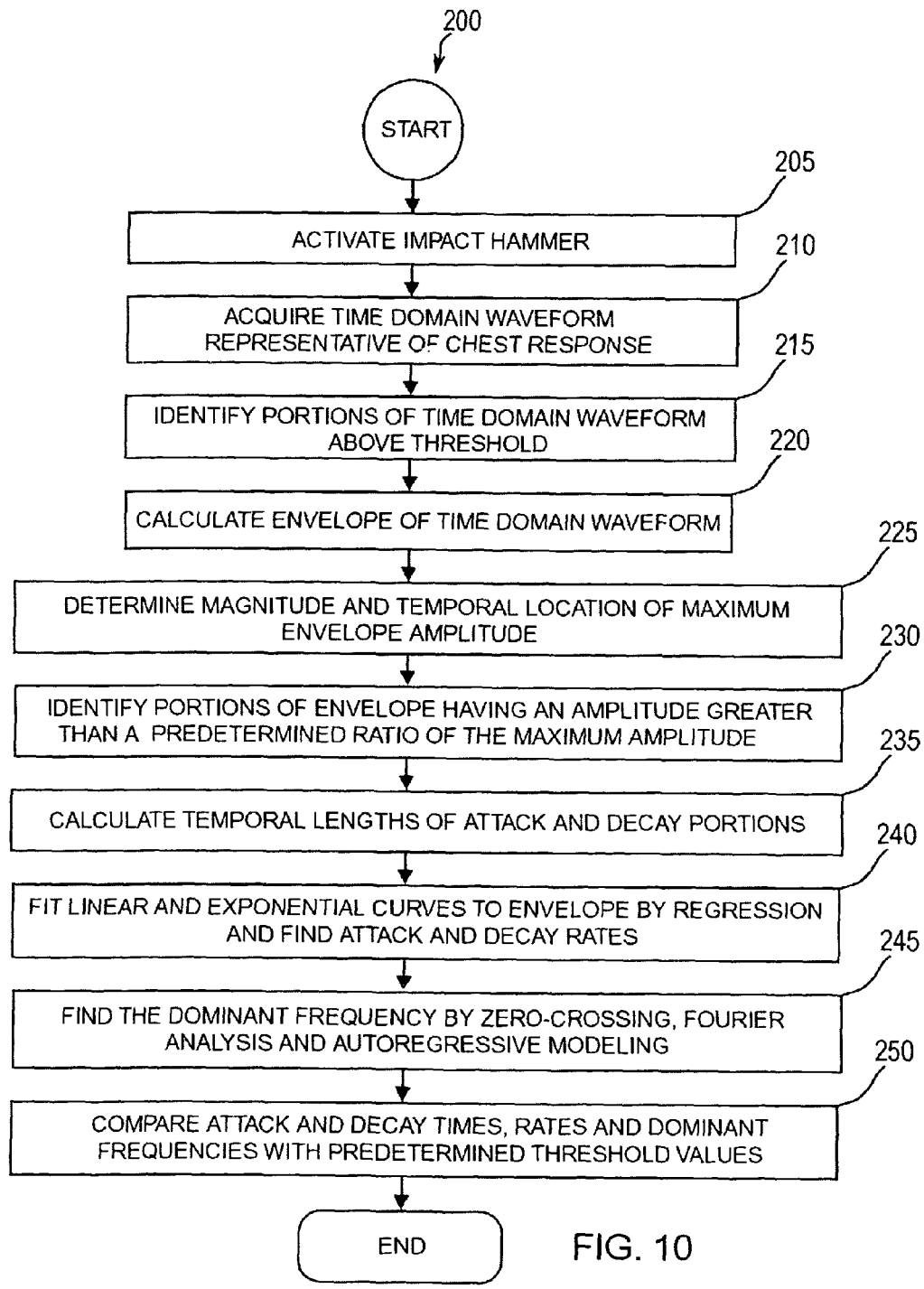
FIG. 10 is a flow diagram representing one method by which the acoustic response characteristics of a patient's chest and lungs may be analyzed using the system shown in FIG. 8.

FIG. 10 is a flow diagram representing one method 200 by which the acoustic response characteristics of a patient's chest and lungs can be analyzed using the system 150 shown in FIG. 8. In block 205, the processing unit 34 activates the impact hammer 152 to impact the chest of the patient 12 and, in block 210, the processing unit 34 receives electrical signals via the microphone 154 and the amplifiers 30 that are representative of vibrations resulting in the patient's chest from the impact of the hammer 152. In block 215, the processing unit 34 monitors the acquired time domain waveform and identifies portions of the time domain waveform that are above a predetermined threshold for subsequent processing. Those portions of the waveform that fall below the predetermined threshold are not processed any further and are considered to be spurious and/or noise-related.

In block 220, the processing unit 34 calculates the envelope of the portions of the time domain waveform identified as above the threshold in block 215. By way of example only, a Hilbert transform or any other envelope calculation technique may be used to calculate the envelope of the time domain waveform. In block 225, the processing unit 34 determines the temporal location and the magnitude of the maximum envelope amplitude and, in block 230, the processing unit 34 identifies portions of the envelope (surrounding the location of the maximum amplitude) having an amplitude greater than a predetermined ratio of the maximum amplitude. For example, the predetermined ratio may be set to 20% so that the portions of the envelope identified in block 230 extend temporally to either side of the maximum envelope value to the points where the envelope amplitude is 20% of the maximum envelope amplitude.

In block 235, the processing unit 34 calculates the temporal lengths of the attack portion of the envelope, which is the identified portion preceding the temporal location of the maximum envelope value, and the decay portion, which corresponds to the identified portion that follows the temporal location of the maximum envelope value. In block 240, the processing unit 34 fits the attack and decay portions of the envelope to linear and/or exponential curves by regression and then uses the results of the regression (i.e., the curve fit) to calculate the attack and decay rates (i.e., the slopes of the fit curves).

In block 245, the processing unit 34 determines the dominant frequency using zero-crossing, Fourier analysis and autoregressive modeling, which are all well known techniques for determining the frequency of a time domain signal. In block 250, the processing unit 34 compares the attack and decay times, attack and decay rates and dominant frequencies with predetermined threshold values. For example, if the dominant frequency is found to be greater than a dominant frequency threshold value associated with an abnormal respiratory condition such as pneumothorax, then the processing unit 34 may send indications to the user via the display 46 that a pneumothorax condition is probably present. Similar comparisons of the decay times and rates to predetermined threshold values associated with one or more different respiratory conditions can be made that result in the indication of a probable diagnosis to the user. Further, the attack and decay times, as well as the dominant frequencies, can be passed through a neural network analysis (similar to that discussed above in connection with FIG. 4) to provide increased confidence in the diagnostic outputs that are presented to the user.

Figure 11:
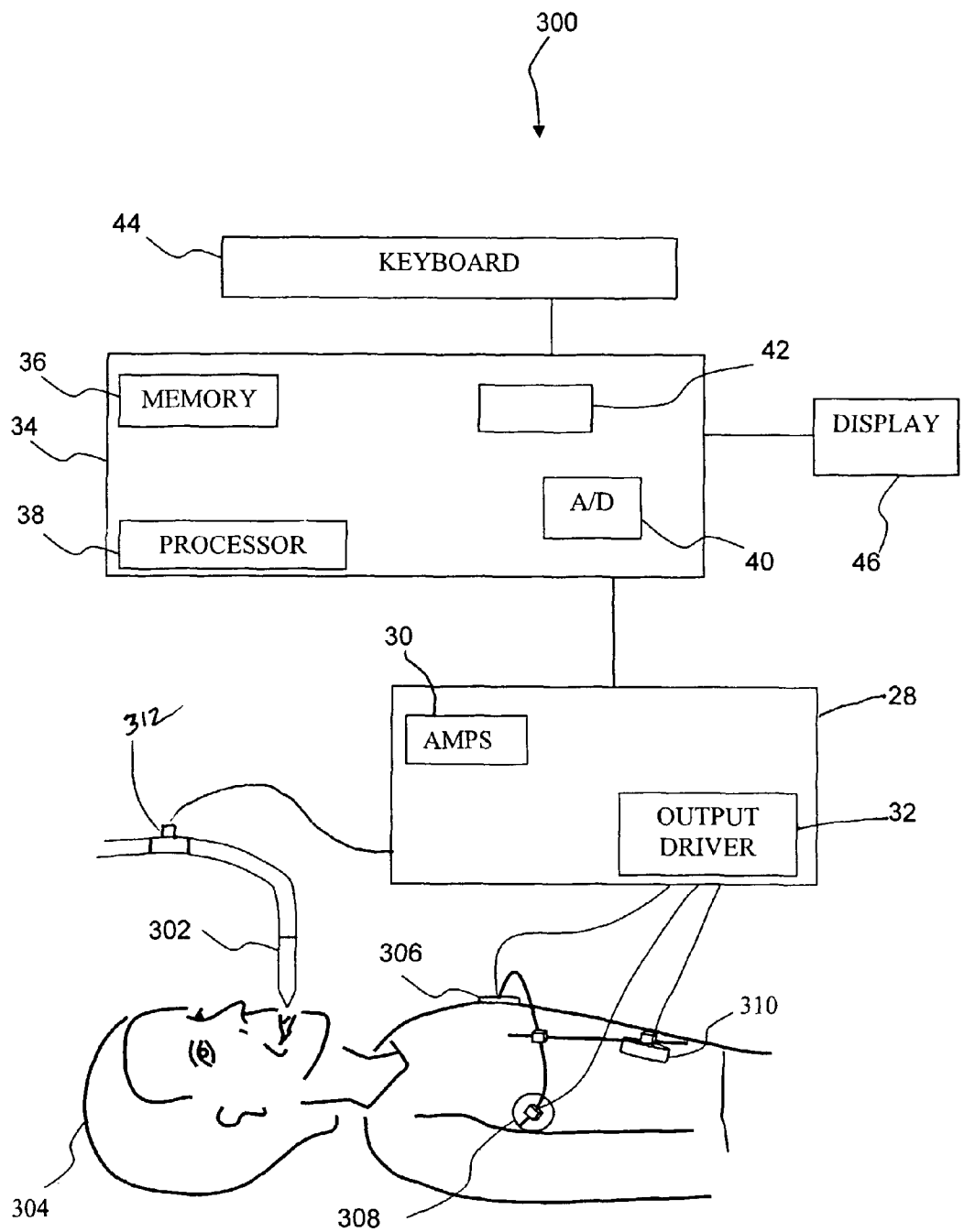
FIG. 11 is an exemplary schematic block diagram illustrating a system for detecting the location of an endotracheal tube within a patient.

FIG. 11 is an exemplary schematic block diagram illustrating a system 300, which is similar to the system 10 shown in FIG. 1, for detecting the placement of an endotracheal tube 302 within a patient 304. The system 300 includes several components that are similar to or the same as those shown and described in connection with FIG. 1 and, thus, are identified using the same reference numerals used in FIG. 1. As shown in FIG. 11, three acoustic sensors 306, 308 and 310 are disposed on or adjacent to the skin surface of the patient 304 to measure ventilation or indigenous breath sounds bilaterally on the chest wall and over the epigastrium or epigastric region of the patient 304. In particular, in the example configuration shown in FIG. 11, the sensors 306 and 308 are bilaterally located on or adjacent to the left and right chest regions preferably, but not necessarily, at the axillary lines at the level of the xyphoid of the patient 304. The abdominal sensor 310 is preferably located over the epigastrium. The sensors 306 and 308 may be identical or similar to the sensors 24 and 26 and, thus, may be electronic stethoscopes or any other type of contact or non-contact microphones or acoustic sensors. As depicted by way of example in FIG. 11, the sensors 306-310 may be coupled to the signal conditioning unit 28, which in turn is coupled to the processing unit 34, both of which are described in detail in connection with FIG. 1 above. While FIG. 11 depicts the sensors 306-310 as being connected to the signal conditioning unit 28 via wires or the like, any other suitable coupling such as, for example, wireless communications, may be used instead. An airflow sensor 312 may optionally be included with the system 300. As described in greater detail below, the airflow sensor 312 may be used to provide ventilation cycle timing information to improve signal-to-noise ratio.

Figure 12:
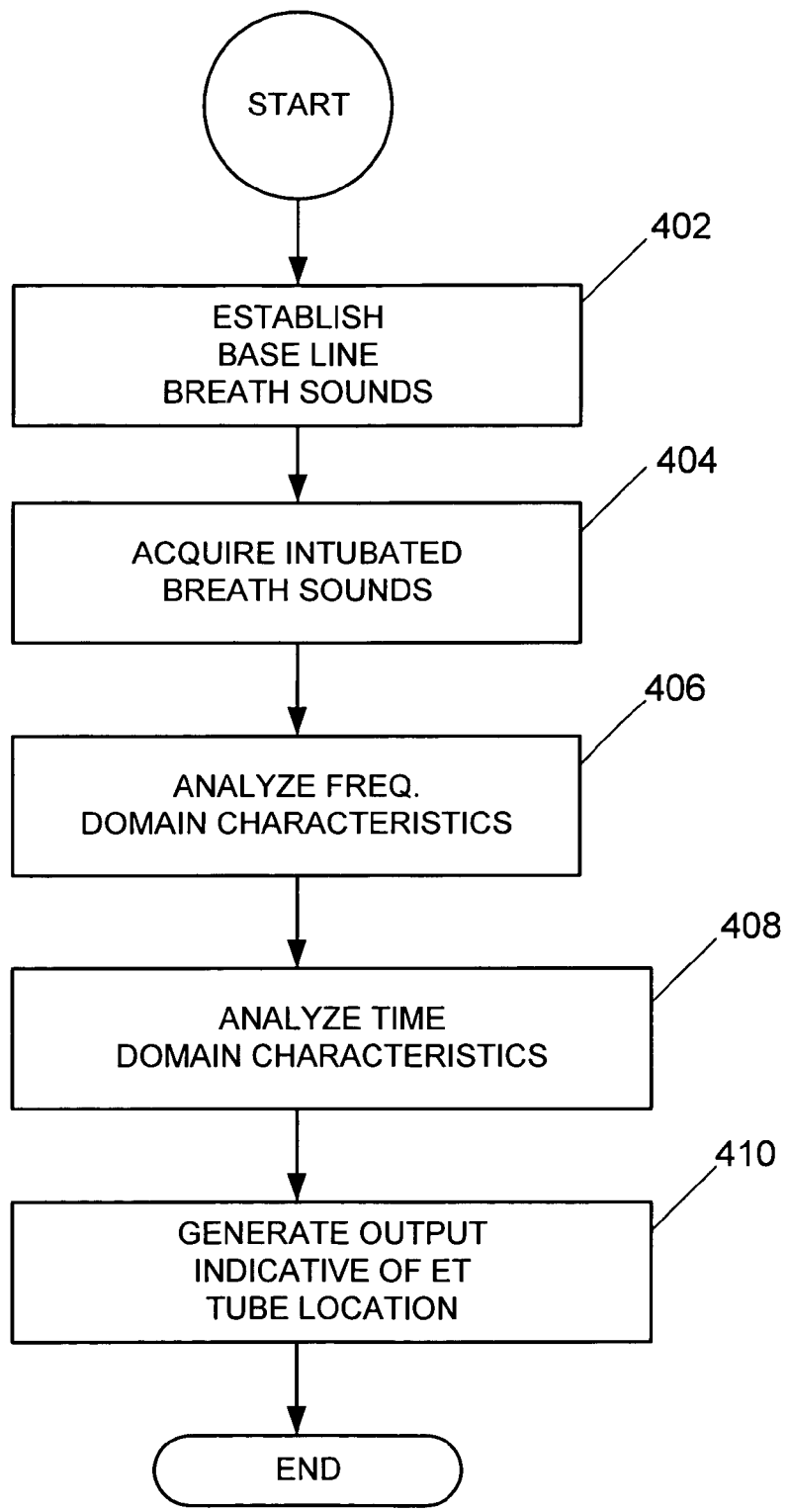
FIG. 12 is a flow diagram representing one method by which the location of an endotracheal tube within a patient may be detected using the system of FIG. 11.

FIG. 12 is a flow diagram that depicts one manner in which the system 300 shown in FIG. 11 may be used to detect ET tube placement or location. In block 402, a baseline for indigenous breath sounds for the patient 304 is established. To establish such a baseline, the patient 304 may be mask ventilated in a known manner and the indigenous breath sounds of the patient 304 may be acquired for three breathing cycles. Of course, establishment of a baseline may be carried out using more or fewer breathing cycles if desired. The baseline time domain waveforms generated by each of the sensors 306-310 may be digitized by the A/D converter 40 and converted into baseline spectral information using a FFT or any other suitable method of converting time domain information into frequency domain information. In any event, the acquired time domain information and the generated frequency domain information may be stored within the memory 36 and processed by the processing unit 34 to generate time domain and frequency domain characteristics such as, for example, time delays and energy ratios representative of the acoustic characteristics of the lungs, trachea and/or other air passages of the patient 304 when in a non-intubated condition. While the baseline acoustic characteristics are described above as being developed by analyzing the breath sounds of the patient 304 during a plurality of breathing cycles while the patient 304 is mask ventilated (i.e., is not intubated), a set of predetermined baseline values may instead be stored in the memory 36 and, if desired, selected for use in subsequent analyses (described below) of the indigenous breath sounds of the patient 304 in an intubated state.

In block 404, the patient 304 is intubated with the ET tube 302 and breath sounds signals are acquired for one or more breathing cycles (e.g., three cycles). In block 406, frequency domain characteristics of the baseline breath sounds information acquired in block 402 and the frequency domain characteristics of the post intubation breath sounds information acquired in block 404 are compared. As described in greater detail below, energy ratios indicative of ET tube placement or location may be calculated. In block 408, the processing unit 34 may compare the time domain or temporal characteristics of the baseline information acquired in block 402 and the post intubation breath sounds information acquired in block 404.

In block 410, the system 300 may generate an output which is indicative of the placement or location of the ET tube 302 within the body of the patient 304. For example, a text message indicating proper or improper placement of the ET tube 302 may be displayed via the display 46 or any other output device. Of course, any other visual and/or audible indications may be provided if desired.

The system 300 shown in FIG. 11 may use adaptive filtering techniques to eliminate unwanted signals due to, for example, environmental noise and heart sounds of the patient 304. Such adaptive filtering techniques may employ an additional acoustic sensor (not shown) that is adapted and positioned to primarily measure the unwanted sounds. Alternatively, the adaptive filtering may be based on identifying and removing correlated components of the signals generated by each of the sensors 306-310 rather than using an additional sensor or sensors to measure sounds, such as heart sounds, that affect the output of the sensors 306-310 substantially equally.

In addition, the system 300 may neglect data segments (i.e., portions of time domain signals acquired from the sensors 306-310) having a relatively low signal-to-noise ratio. In particular, a predetermined threshold value associated with a lower limit for airflow and/or breath sounds signal amplitude may be compared to acquired values and, if the acquired values are below the threshold value, then such acquired values and/or the segments of data associated with such acquired values may be ignored or discarded (i.e., not used in any subsequent analysis). For example, the processing unit 34 may ignore the data segments between about 1.25 and 2.00 seconds of the signal shown in FIG. 18a, thereby eliminating the use of low signal-to-noise ratio portions of the signal shown in FIG. 18a in any subsequent spectral and/or time domain analyses.

Still further, the system 300 may store parameters for selected patients and may use these stored parameters for subsequent comparison to information gathered for those same patients at later times. In this manner, the system 300 may be adapted to increase its accuracy for particular patients by optimizing analysis phases and/or frequency bands for those patients. By way of example only, the baseline values for a patient being continuously monitored may be updated each time a clinician or other operator confirms a proper ET tube placement or location and instructs the system 300 to update the breath sounds parameters for that patient by pressing, for example, a reset or baseline store button associated with the system 300.

The system 300 may also store a template of typical signal characteristics of breath sounds to detect adventitious sounds. These signal characteristics are usually, but not necessarily, the time envelope and spectral distributions of breath sounds. Because detecting adventitious sounds is suggestive of need for airway suction, the system 300 may then alert the user or other operator of the system 300 that airway suction is needed to prevent a false reading. Of course, other adventitious breath sound characteristics can be used without departing from the scope of the invention.

The system 300 shown in FIG. 11 may also provide an audible and/or visual indication of an impending or current malfunction such as, for example, improper attachment or coupling of the sensors 306-310 to the patient 304, low tidal volumes (e.g., due to severe asthma or improper connecting tubes), etc.

Further, while the system 300 is described herein as based on digital signal analysis techniques, it should be recognized that the various techniques described herein may be implemented using primarily analog circuitry and analog signal analysis techniques. For example, analog filter banks may be used to extract signal information (e.g., signal amplitude, power, etc.) from predetermined frequency bands and such extracted signal information may be processed to produce one or more outputs indicative of ET tube placement or location.

Figure 13:
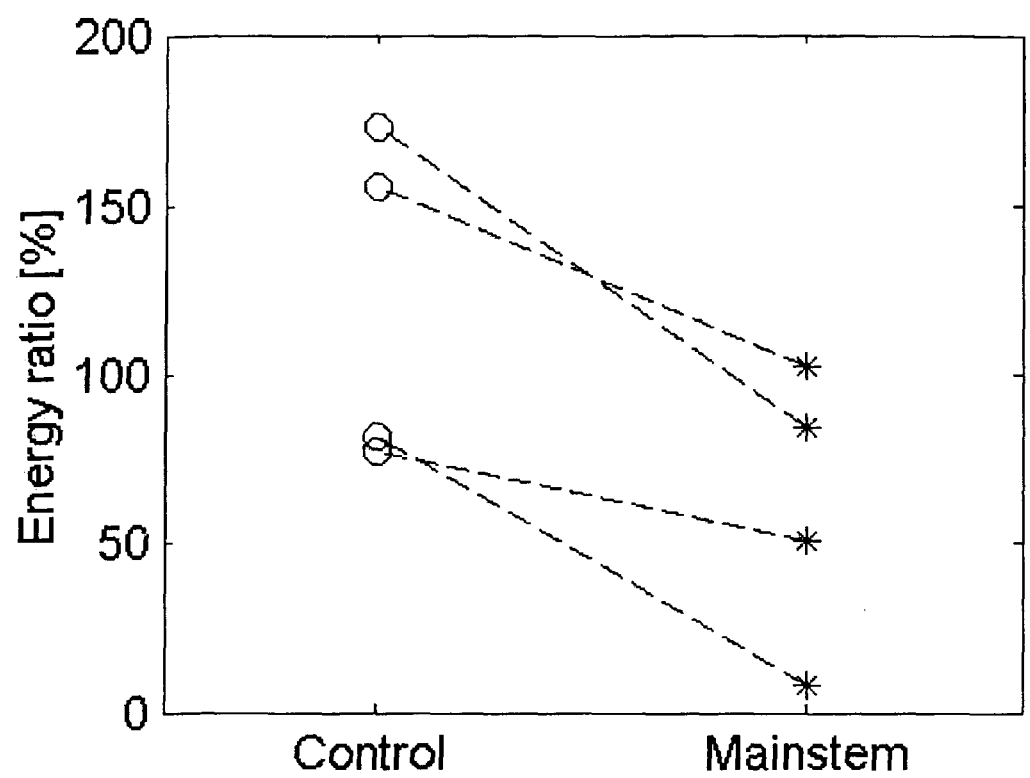
FIG. 13 is an exemplary graphical representation showing breath sounds energy ratios between the left and right chest regions of four patients in a mainstem intubation state and a control state.
Figure 14:
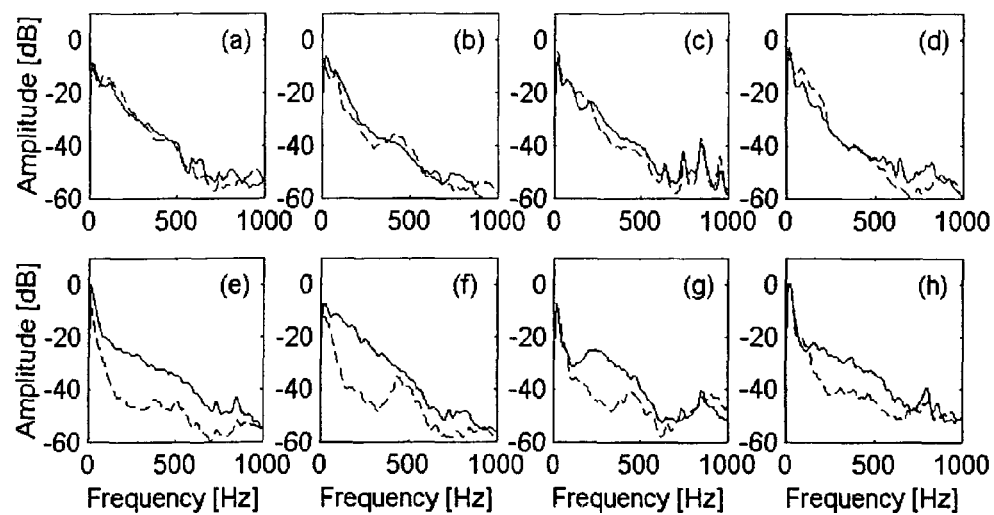
FIGS. 14a-d are exemplary graphical representations of the spectra of breath sounds measured at the right and left chest regions of four tracheally intubated patients.
FIGS. 14e-h are exemplary graphical representations of the spectra of breath sounds measured at the right and left chest regions of four mainstem intubated patients.

FIG. 13 is an exemplary graphical representation showing the breath sounds energy ratios between the left and right chest sensors (i.e., the sensors 306 and 308 of the system 300) between 0 Hz and 4000 Hz for four patients, each of which is tested in a manner identical to that shown in connection with the patient 304 of FIG. 11. As shown in FIG. 13, the energy ratios for each of the patients when tracheally intubated (represented by the circles) is substantially greater than the energy ratio for each of the patients (where energy ratio data for a particular patient is connected by the dashed lines) when in a mainstem intubation condition (represented by the stars). In other words, for a particular patient, mainstem intubation, which is an undesirable ET tube placement or location condition, may be detected by a relatively lower energy ratio between left and right chest sensors.

However, as can also be seen from FIG. 13, inter-subject variability is sufficiently large so that the ranges of tracheal intubation values and mainstem intubation energy ratios overlap for a plurality of patients or subjects. Thus, from FIG. 13 it is clear that a mainstem intubation condition for a particular patient cannot be easily recognized without comparison to the acoustic characteristics associated with that patient when properly tracheally intubated. In fact, as depicted in FIG. 13, the two highest mainstem energy ratio values represent a relatively high degree of symmetry between the left and right chest sensors 306 and 308 (i.e., the energy ratios are near to 100% which indicates that the signals received from the sensors 306 and 308 are substantially equal), which, in the absence of knowledge of the energy ratios for those patients when properly tracheally intubated, would likely lead to a false conclusion that the ET tube 302 is correctly placed or located in the trachea of the patient 304. Because the energy ratio for a tracheally intubated patient is substantially similar to the baseline energy ratio for that patient (i.e., the energy ratio associated with a mask ventilated or non-intubated condition for that patient), a comparison of the calculated energy ratio for the patient to the baseline value for that patient may be used to identify a mainstem intubation condition.

FIGS. 14a-d are exemplary graphical representations of the spectra of breath sounds measured at the right and left chest regions of four tracheally intubated patients, and FIGS. 14e-h are exemplary graphical representation of the spectra of breath sounds measured at the right and left chest regions of the same four patients when mainstem intubated. As can be seen in FIGS. 14a-h, a mainstem intubation condition is generally characterized by an asymmetry between the spectral energy levels associated with the right and left chest sensors 306 and 308 (represented by the solid and dashed lines, respectively). In particular, in a tracheal intubation condition, the spectral amplitudes for the right and left chest regions are relatively similar over a wide range of frequencies. In contrast, in a mainstem intubation condition, there are relatively large and consistent amplitude differences between the right and left chest regions, particularly in the 200 Hz to 500 Hz range. In fact, for each of the test subjects shown in FIGS.

14*e-h* the maximum difference exceeds 20 dB, which represents a tenfold amplitude difference and a one-hundred-fold energy difference.

Figure 15:
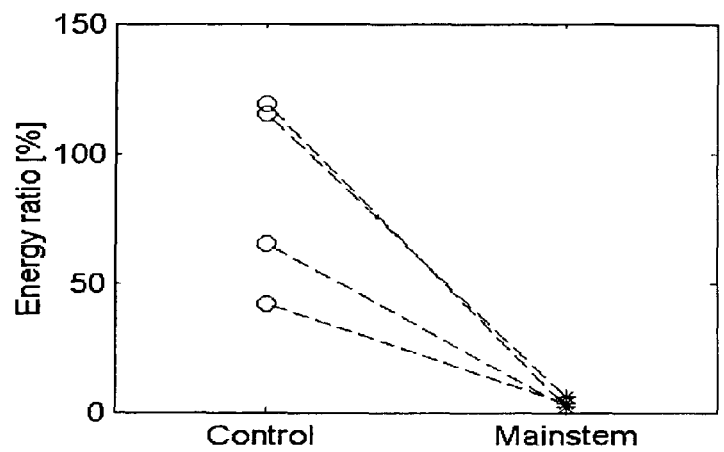
FIG. 15 is an exemplary graphical representation of the breath sounds energy ratios for four patients having a tracheal intubation and a mainstem intubation.
Figure 16:
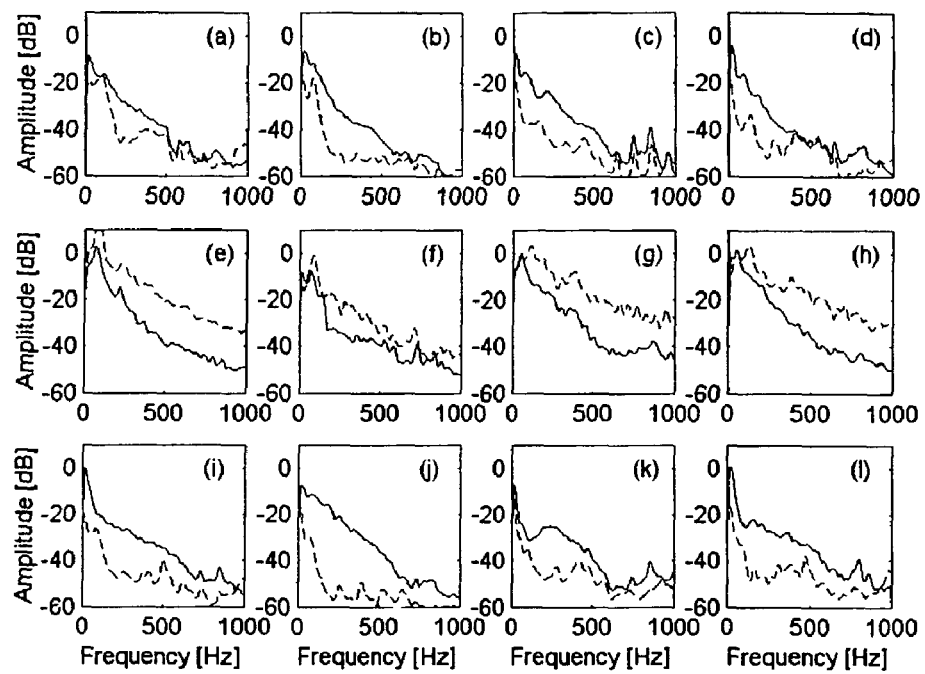
FIGS. 16a-d are exemplary graphical representations of the breath sounds spectra measured at the right chest and epigastric regions of four tracheally intubated patients.
FIGS. 16e-h are exemplary graphical representations of the breath sounds spectra measured at the right chest and epigastric regions of four esophageally intubated patients.
FIGS. 16i-l are exemplary graphical representations of the breath sounds spectra measured at the right chest and epigastric regions of four mainstem intubated patients.

The spectral asymmetry depicted in FIGS. 14*e-h* may be represented by a single parameter such as, for example, by calculating the total energy within a fixed frequency range (e.g., 200 to 500 Hz) for the left and right chest regions and calculating the ratio of the these total energy values. As shown in FIG. 15, the energy ratio of the tracheally intubation states shown in FIGS. 14*a-d* are all greater than about 43%, which is at least seven times higher than the energy ratios (all of which are less than 6%) in the mainstem intubation states shown in FIGS. 14*e-h*. Owing to the lack of overlap between the energy ratios for tracheal and mainstem intubation states for the selected frequency range (i.e., 200 to 500 Hz), a threshold value in the 8% to 43% range may be used by the system 300 (at, for example, block 410) to distinguish between the two states. In fact, the large degree of separation between the tracheal and mainstem intubation states shown in FIGS. 14*a-h* may eliminate the need for baseline measurements for some applications.

While, as depicted in FIGS. 14*a-h* and FIG. 15, the ratio of spectral energies may be useful in detecting the location of an ET tube, other spectral analysis techniques may be used instead or in addition to those depicted in connection with FIGS. 14*a-h* and FIG. 15. For example, the mean spectral difference between the different states in selected frequency bands can be used. As shown in FIGS. 14*a-h*, the mean spectral difference is smallest for tracheal intubation and large for mainstem intubation.

FIGS. 16*a-l* are exemplary graphical representations of the breath sounds spectra measured at the right chest (solid lines) and epigastric regions (dashed lines) of four patients in a tracheal intubation state (FIGS. 16*a-d*), an esophageal intubation state (FIGS. 16*e-h*) and a mainstem intubation state (FIGS. 16*i-l*). As can be seen from FIGS. 16*a-l*, in the tracheal and mainstem intubation states the breath sounds detected by the epigastric region sensor (e.g., the sensor 310 shown in FIG. 11) are lower than the sounds detected by the right chest sensor (e.g., the sensor 308 shown in FIG. 11) for substantially all of the frequency range of 0 Hz to 1000 Hz, particularly above 150 Hz.

Figure 17:
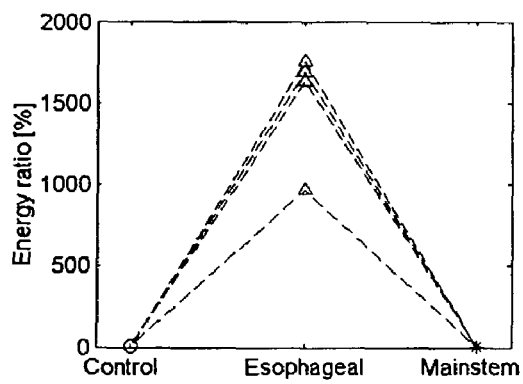
FIG. 17 is an exemplary graphical representation of breath sounds energy ratios between the epigastrium and right chest regions for four patients in tracheal, esophageal and mainstem intubation states.

FIG. 17 is an exemplary graphical representation of breath sounds energy ratios between the epigastrium and right chest regions for the four patients represented in FIGS. 16*a-l* in the tracheal, esophageal and mainstem intubation states. As shown in FIG. 17, in the tracheal and mainstem intubation states, breath sounds heard over the epigastric region is minimal (i.e., the energy ratios are less than 9% and 4% in the tracheal and mainstem intubation states, respectively). However, with the ET tube 302 located in the esophagus of the patient 304, the energy ratios increase to at least 950%. Such a relatively large difference between the energy ratio in the esophageal intubation state and the energy ratios of the tracheal intubation states and the mainstem intubation states (i.e., greater than 100 times in the tracheal intubation state and 240 times in the mainstem intubation state), indicates that the esophageal intubation state can be readily distinguished from mainstem and tracheal intubation states.

Figure 18:
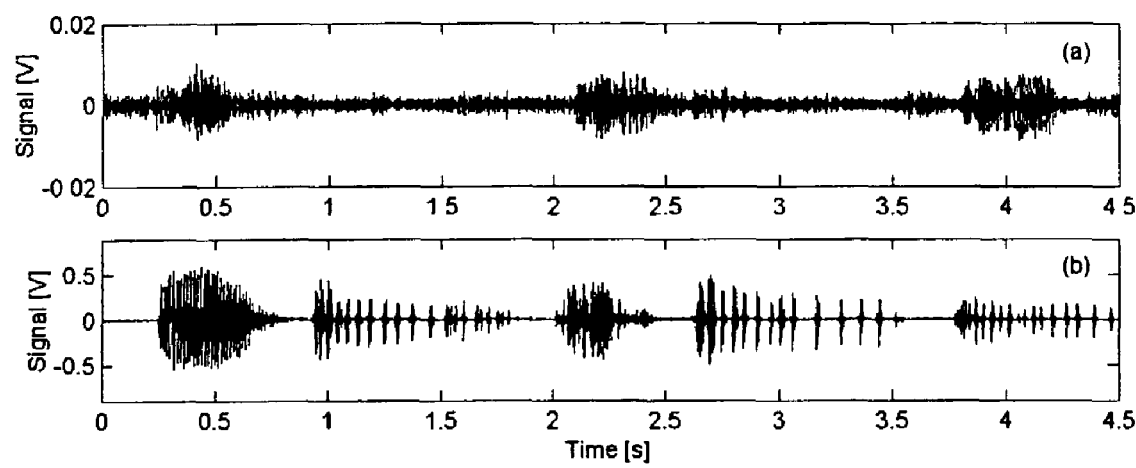
FIG. 18a is an exemplary graphical representation of a signal generated by an acoustic sensor located in the epigastric region of a tracheally intubated patient.
FIG. 18b is an exemplary graphical representation of a signal generated by an acoustic sensor located in the epigastric region of an esophageally intubated patient.

FIG. 18*a* is an exemplary graphical representation of a signal generated by an acoustic sensor (e.g., the sensor 310 shown in FIG. 11) disposed adjacent to the epigastric region of a tracheally intubated patient, and FIG. 18*b* is an exemplary graphical representation of a signal generated by an acoustic sensor located in the epigastric region in an esophageally intubated patient. In addition to the relatively large amplitude differences, there are temporal characteristic differences between the sounds generated in the epigastric region of a tracheally intubated patient and an esophageally intubated patient. The epigastric region acoustic characteristics of a mainstem intubated patient are similar to those of a tracheally intubated patient and, thus, are not shown.

The signal waveforms shown in FIGS. 18*a* and 18*b* each contain three breathing cycles or ventilation events, which begin at approximately 0.25, 2, and 3.75 seconds. The amplitudes, the time histories and the durations of each epigastric acoustic event may differ between tracheally intubated and esophageally intubated patients. For example, the signal amplitude of the epigastric region sensor is substantially lower in a tracheally intubated patient than in an esophageally intubated patient. Note the vertical axis of the graph shown in FIG. 18*a* is fifty times more resolved than the vertical axis of the graph shown in FIG. 18*b*. In addition, the breath sounds events for tracheally intubated patients are shorter than those in esophageally intubated patients. Furthermore, as can be seen in FIG. 18*b*, the longer breath sounds events associated with esophageally intubated patients typically include a plurality of intermittent sub-events, which begin with a main event and which are followed by a plurality of (e.g., ten to twenty) shorter sound events. Still further, the time domain epigastric region sensor signals for esophageally intubated patients demonstrate substantially wider inter-event amplitude variability than those obtained from the epigastric region sensor of a tracheally intubated patient. The various temporal differences between the epigastric region sounds generated (and detected) within a tracheally intubated patient and an esophageally intubated patient may be used to further increase the sensitivity and specificity of the system 300 shown in FIG. 11. For example, the system 300 may quantify inter-event variability by calculating the envelopes of the time domain signals (e.g., those signals shown in FIGS. 18*a* and 18*b*) using a Hilbert transform and the root mean square (RMS) of the envelope among ventilation or breathing cycles following time alignment of the signals. There are other approaches to quantifying inter-event variability such as, for example, cross correlation of the signal envelopes for breath cycle pairs, calculating the RMS of the spectrum of the breath cycles, calculating the RMS of the time dependent spectra, wavelet coefficients, and/or oscillations of the signal envelope during the breathing or ventilation cycles. In any event, a high inter-event or intra-event variability may be indicative of esophageal intubation.

Figure 19:
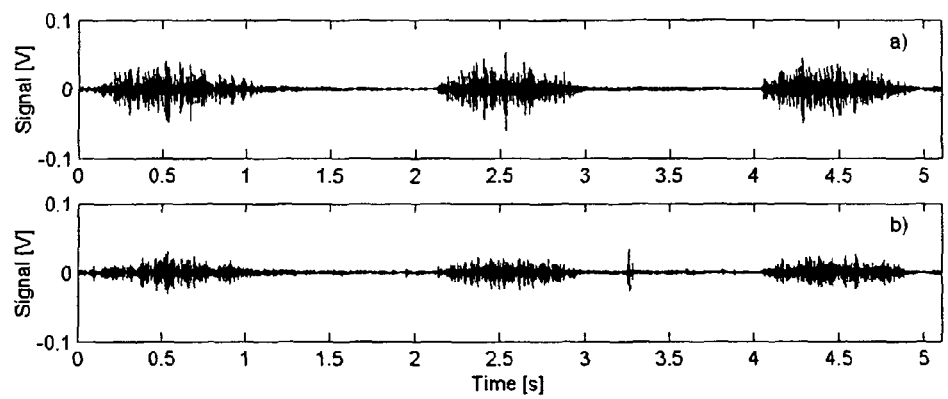
FIG. 19a is an exemplary graphical representation of a time domain signal generated as a result of breath sounds in a patient's right chest region while tracheally intubated.
FIG. 19b is an exemplary graphical representation of a signal generated as a result of breath sounds in a patient's left chest region while tracheally intubated.
Figure 20:
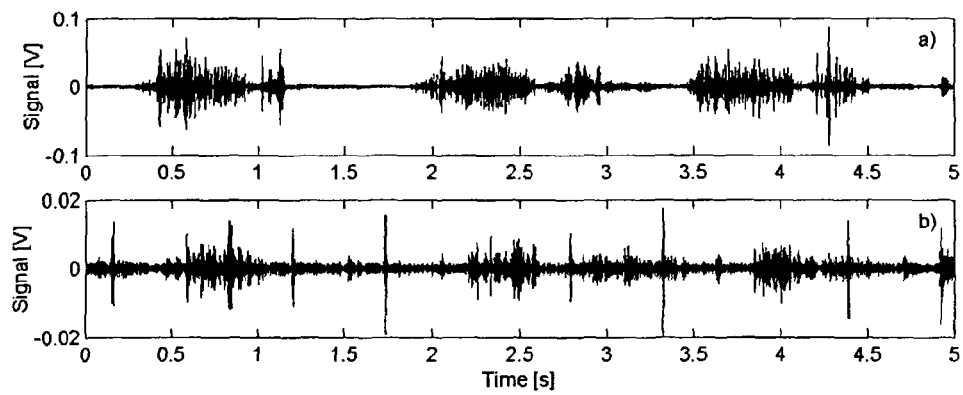
FIG. 20a is an exemplary graphical representation of a signal generated as a result of breath sounds in a patient's right chest region while tracheally intubated and FIG. 20b is an exemplary graphical representation of a signal generated as a result of breath sounds in a patient's left chest region while tracheally intubated.

FIGS. 19*a* and 19*b* are exemplary graphical representations of signals generated as a result of breath sounds in a patient's right and left chest regions, respectively, during tracheal intubation. FIGS. 20*a* and 20*b* are exemplary graphical representations of signals generated as a result of breath sounds in a patient's right and left chest regions, respectively, during mainstem intubation. As can be seen from FIGS. 19 and 20, the onset of the breath sound signal from the left chest region is delayed in the case of mainstem intubation. Thus, the system 300 may be programmed to use a Hilbert transform to estimate the signal envelope and to thereby determine the start and end time of the breath sounds signals via amplitude thresholding. For example, the event start and end points may be defined as the points at which the signal is about twenty percent of its maximum value. The system 300 may then calculate the onset time delay between the right and left chest sensors and, if a substantial delay (e.g., greater than about 25 milliseconds) is detected, the system 300 may report a possible ET tube misplacement in the mainstem of the patient. Of course, the unventilated side of the chest of the patient would demonstrate the delayed onset.

In other embodiments, the airflow sensor 312 may be included to provide ventilation cycle timing information. In the case the optional airflow sensor 312 is provided by the system 300, the system 300 may use the signals from the airflow sensor 312 to determine the beginning and end of each breathing, ventilation or respiration cycle of the patient 304. Such ventilation cycle timing information may be used to facilitate the inter- and intra-event analyses described above. The system 300 may also calculate the time-dependent spectra during each cycle and may average the spectra for several ventilation or respiration cycles after time alignment to determine the average time-dependent spectrum during each cycle. In this manner, the system 300 may provide better estimates of the time-dependent spectra than would otherwise be possible using only information from a single cycle. The system 300 may also calculate energy ratios for different phases (e.g., five phases with equal time for each) during the respiration cycle. An example of one phase of a respiration cycle that yields optimal diagnostic accuracy is the phase that corresponds to high sound amplitudes because of the increased signal-to-noise-ratio. Other optimal phases of the ventilation or respiration cycle may be determined as the system 300 is used on a larger number of subjects.

The use of the airflow sensor 312 described herein is only an exemplary manner of providing a timing signal or information associated with patient respiration cycles. Other manners of determining the timing of patient respiration can be used without departing from the scope of the invention. For example, a pressure transducer sensing the airflow stream within a patient can also provide the timing signal.

Additionally, when a pressure transducer is combined with an airflow transducer, information associated with the compliance of a patient's lungs may be determined. A bi-directional airflow meter may also be used to report decreased expiratory phase of ventilation that is likely encountered during esophageal intubation.

Still further, the airflow sensor 312 may be used to subtract no-airflow spectra from the ventilation spectra to increase the signal-to-noise-ratio of the acquired data and thereby improving diagnostic accuracy. The system 300 may acquire no-airflow data by acquiring an extra segment of data such as, for example, a one second long measurement of breath sounds at no-flow. Still further, the system 300 may also include an indicator signal (e.g. a blinking light) that alerts the practitioner of the acquisition time, which may be helpful in allowing the extra time for acquiring the no-airflow data. Of course, a more sophisticated indicator (e.g. a LCD display) can be added to the system 300 to report progression of the acquisition and processing and to provide step-by-step instructions during use of the system 300.

While the mainstem intubation examples described herein refer to overadvancement of an ET tube into the right mainstem bronchus, over-advancement into the left mainstem bronchus is also possible and may be treated similarly.

If implemented in software, the functional blocks and routines discussed herein may be stored in any computer readable memory such as on a magnetic, an optical, or other storage medium, in a RAM or ROM of a computer, controller, etc. Likewise, this software may be modulated on a carrier and delivered to a user or a device via any known or desired delivery method including, for example, over a communication channel such as a telephone line, the Internet, etc.

While the invention has been described with reference to specific examples, which are intended to be illustrative only and not to be limiting of the invention, it will be apparent to those of ordinary skill in the art that changes, additions or deletions may be made to the disclosed embodiments without departing from the spirit and the scope of the invention. For example, while the system and method described herein is described in connection with detecting ET tube location in a human patient, it should be understood that the system and method may be more generally applied to other organisms. Additionally, the system and method described herein may be used for guiding initial intubations as well as continuous monitoring of ET tube locations after initial positioning.

What is claimed is:

1. A method of detecting an endotracheal tube location within a body, the method comprising:
   electronically detecting indigenous breath sounds emanating from the body, including receiving a first signal from a first acoustic sensor at a first location of the body and a second signal from a second acoustic sensor at a second location of the body;
   electronically processing the detected indigenous breath sounds to calculate a first acoustic energy corresponding to the first location using the first signal and a second acoustic energy corresponding to the second location using the second signal, wherein each of the acoustic energies corresponds to substantially the same time interval;
   calculating an acoustic energy ratio of the first and second acoustic energies, wherein the acoustic energy ratio is representative of an acoustic characteristic of the body associated with the endotracheal tube location within the body; and
   electronically generating an output indicative of the endotracheal tube location within the body based on the acoustic energy ratio.

2. The method of claim 1, wherein at least one of the first acoustic sensor or the second acoustic sensor is disposed adjacent to one of a chest region of the body or an epigastric region of the body.

3. The method of claim 1, wherein the first acoustic sensor is disposed adjacent to a left side chest region of the body and the second acoustic sensor is disposed adjacent to a right side chest region of the body.

4. The method of claim 1, wherein the acoustic energy ratio is a spectral energy ratio.

5. The method of claim 4, wherein calculating the spectral energy ratio includes converting the detected indigenous breath sounds into digital information and using a fast Fourier transform to calculate the spectral energy ratio.

6. The method of claim 4, wherein calculating the spectral energy ratio includes dividing a first spectral energy value associated with a chest region of the body by a second spectral energy value associated with an epigastric region of the body.

7. The method of claim 1, wherein electronically processing the detected indigenous breath sounds further comprises calculating one of a mean spectral difference or a time delay.

8. The method of claim 1, wherein electronically generating the output indicative of the endotracheal tube location within the body based on the acoustic energy ratio includes comparing the acoustic energy ratio to a baseline value associated with a non-intubated condition of the body.

9. The method of claim 1, wherein electronically generating the output indicative of the endotracheal tube location within the body based on the acoustic energy ratio representative of the acoustic characteristic of the body includes generating one of a visual or an audible indication of the endotracheal tube location.

10. The method of claim 1, wherein electronically generating the output indicative of the endotracheal tube location within the body based on the acoustic energy ratio representative of the acoustic characteristic of the body includes generating an output indicative of one of a tracheal location, an esophageal location or a mainstem location.

11. The method of claim 1, further including electronically detecting ventilation cycle timing information of the body and using the ventilation cycle timing information to process the detected indigenous breath sounds.

12. The method of claim 1, wherein electronically processing the detected indigenous breath sounds to calculate the acoustic energy ratio representative of the acoustic characteristic of the body associated with the endotracheal tube location within the body includes discarding data associated with a portion of the detected indigenous breath sounds having a low signal-to-noise ratio.

13. The method of claim 12, wherein discarding data associated with the portion of the detected indigenous breath sounds having a low signal-to-noise ratio includes discarding the data based on a predetermined threshold value.

14. The method of claim 1, wherein electronically detecting the indigenous breath sounds emanating from the body includes detecting indigenous breath sounds emanating from an epigastric region of the body.

15. The method of claim 14, wherein electronically processing the detected indigenous breath sounds to calculate the acoustic energy ratio representative of the acoustic characteristic of the body associated with the endotracheal tube location within the body includes calculating a temporal characteristic of the indigenous breath sounds emanating from the epigastric region of the body.

16. The method of claim 15, wherein electronically generating the output indicative of the endotracheal tube location within the body based on the acoustic energy ratio representative of the acoustic characteristic of the body includes generating an output indicative of an esophageal location of the endotracheal tube within the body based on the temporal characteristic of the indigenous breath sounds emanating from the epigastric region of the body.

17. The method of claim 1, wherein electronically detecting the indigenous breath sounds emanating from the body includes electronically detecting indigenous breath sounds associated with a left chest region of the body and detecting indigenous breath sounds associated with a right chest region of the body.

18. The method of claim 17, wherein electronically processing the detected indigenous breath sounds includes calculating a time delay between the indigenous breath sounds associated with the left chest region and the indigenous breath sounds associated with the right chest region.

19. The method of claim 18, wherein electronically generating the output indicative of the endotracheal tube location within the body includes generating an output indicative of a mainstem location of the endotracheal tube within the body based on the time delay between the indigenous breath sounds associated with the left chest region and the indigenous breath sounds associated with the right chest region.

20. The method of claim 1, further including generating a low signal level indication in response to a determination that the detected indigenous breath sounds are below a predetermined threshold value.

21. The method of claim 1, further including generating a baseline value for comparison to the acoustic energy ratio representative of the acoustic characteristic.

22. The method of claim 21, wherein generating the baseline value includes generating the baseline value based on one of historical breath sounds data, a mask-ventilated condition of the body, or a tracheally intubated condition of the body.

23. The method of claim 1, wherein electronically processing the detected indigenous sounds to calculate the acoustic energy ratio representative of the acoustic characteristic of the body includes using an adaptive filtering technique to filter noise.

24. The method of claim 1, wherein the first signal received from the first sensor and the second signal received from the second sensor are in the same frequency band.

25. A system for use in detecting an endotracheal tube location within a body, the system comprising:
a first acoustic sensor to electronically detect indigenous breath sounds emanating from a first location of the body;
a second acoustic sensor to electronically detect indigenous breath sounds emanating from a second location of the body;
a processing unit to receive a first signal from the first acoustic sensor and a second signal from the second acoustic sensor and to electronically process the first signal and the second signal to calculate a first acoustic energy corresponding to the first location using the first signal and a second acoustic energy corresponding to the second location using the second signal, wherein each of the acoustic energies corresponds to substantially the same time interval and to calculate an acoustic energy ratio based on the first and second acoustic energies, wherein the acoustic energy ratio is representative of an acoustic characteristic of the body associated with the endotracheal tube location within the body; and
an output device to electronically generate an output indicative of the endotracheal tube location within the body based on the acoustic energy ratio.

26. The system of claim 25, wherein at least one of the first acoustic sensor or the second acoustic sensor is to be disposed adjacent one of a chest region of the body or an epigastric region of the body.

27. The system of claim 25, wherein the first acoustic sensor is to be disposed adjacent to a left side chest region of the body and the second acoustic sensor is to be disposed adjacent to a right side chest region of the body.

28. The system of claim 25, wherein the acoustic energy ratio is a spectral energy ratio.

29. The system of claim 28, wherein the processing unit is to calculate the spectral energy ratio by converting the first signal and the second signal into digital information and using a fast Fourier transform to convert the digital information into spectral information.

30. The system of claim 28, wherein the processing unit is to calculate the spectral energy ratio by dividing a first spectral energy value associated with a chest region of the body by a second spectral energy value associated with an epigastric region of the body.

31. The system of claim 25, wherein the processing unit is to further calculate one of a mean spectral difference or a time delay.

32. The system of claim 25, wherein the output indicative of the endotracheal tube location within the body is based on a comparison of the acoustic energy ratio representative of the acoustic characteristic of the body to a baseline value associated with a non-intubated condition of the body.

33. The system of claim 25, wherein the output device is to generate one of a visual or an audible indication of the endotracheal tube location.

34. The system of claim 25, wherein the output device is to generate one of an output indicative of one of a tracheal location, an esophageal location or a mainstem location.

35. The system of claim 25, further including an airflow sensor that is to electronically detect ventilation cycle timing information of the body, and wherein the processing unit is to use the ventilation cycle timing information to process the first signal and the second signal.

36. The system of claim 25, wherein the processing unit is to discard data associated with a portion of the first signal or the second signal having a low signal-to-noise ratio.

37. The system of claim 36, wherein the processing unit is to discard the data based on a predetermined threshold value.

38. The system of claim 25, wherein at least one of the first acoustic sensor or the second acoustic sensor is to electronically detect the indigenous breath sounds emanating from an epigastric region of the body.

39. The system of claim 25, wherein the processing unit is to calculate the acoustic energy ratio representative of the acoustic characteristic of the body associated with the endotracheal tube location within the body by calculating a temporal characteristic of the first signal or the second signal based on the acoustic characteristic.

40. The system of claim 39, wherein the output device is to electronically generate an output indicative of an esophageal location of the endotracheal tube within the body.

41. The system of claim 25, wherein the first acoustic sensor is to detect indigenous breath sounds associated with a left chest region of the body and the second acoustic sensor that is to detect indigenous breath sounds associated with a right chest region of the body.

42. The system of claim 41, wherein the processing unit is to calculate a time delay between the indigenous breath sounds associated with the left chest region and the indigenous breath sounds associated with the right chest region.

43. The system of claim 42, wherein the output device is to electronically generate an output indicative of a mainstem location of the endotracheal tube within the body based on the time delay.

44. The system of claim 25, wherein the output device is to electronically generate a low signal level indication in response to a determination that the first signal second signal is below a predetermined threshold value.

45. The system of claim 25, wherein the processing unit is to generate a baseline value for comparison to the acoustic energy ratio representative of the acoustic characteristic.

46. The system of claim 45, wherein the processing unit is to generate the baseline value by generating the baseline value based on one of historical breath sounds data, a mask-ventilated condition of the body, or a tracheally intubated condition of the body.

47. The system of claim 25, wherein the processing unit is to calculate the acoustic energy ratio representative of the acoustic characteristic of the body using an adaptive filtering technique to filter noise.

48. The system of claim 25, wherein the first signal and the second signal are in the same frequency band.

\* \* \* \* \*